United States Patent [19]

Black et al.

[11] 4,000,302
[45] Dec. 28, 1976

[54] PHARMACEUTICAL COMPOSITIONS AND METHODS OF INHIBITING H-1 AND H-2 HISTAMINE RECEPTORS

[75] Inventors: James Whyte Black, Hemel Hempstead; Michael Edward Parsons, St. Albans, both of England

[73] Assignee: Smith Kline & French Laboratories Limited, Welwyn Garden City, England

[22] Filed: Apr. 16, 1975

[21] Appl. No.: 568,481

Related U.S. Application Data

[63] Continuation-in-part of Ser. No. 349,151, April 9, 1973, Pat. No. 3,894,151.

[52] U.S. Cl. .............................. 424/273; 424/246; 424/250; 424/251; 424/263; 424/267; 424/269; 424/274; 424/325
[51] Int. Cl.² ...................................... A61K 31/415
[58] Field of Search ................................... 424/273

[56] References Cited

UNITED STATES PATENTS

| | | | |
|---|---|---|---|
| 3,354,174 | 11/1967 | Bell | 260/309.2 |
| 3,868,457 | 2/1975 | Black et al. | 424/270 |
| 3,897,444 | 7/1975 | Durant et al. | 424/270 |

*Primary Examiner*—Norman A. Drezin
*Attorney, Agent, or Firm*—Joan S. Keps; Richard D. Foggio; William H. Edgerton

[57] ABSTRACT

Pharmaceutical compositions and methods of inhibiting H-1 and H-2 histamine receptors by administering an antihistamine and an H-2 histamine receptor inhibitor. Exemplary of the antihistamine in the compositions and methods of this invention is mepyramine and exemplary of the H-2 histamine receptor inhibitor is N-cyano-N'-methyl-N''-[2-((4-methyl-5-imidazolyl)-methylthio)ethyl]guanidine.

18 Claims, No Drawings

PHARMACEUTICAL COMPOSITIONS AND METHODS OF INHIBITING H-1 AND H-2 HISTAMINE RECEPTORS

This application is a continuation-in-part of Serial No. 349,151 filed Apr. 9, 1973, now U.S. Pat. No. 3,894,151.

This invention relates to pharmaceutical compositions having H-1 and H-2 histamine receptor inhibiting activity and methods of inhibiting H-1 and H-2 histamine receptors. The compositions comprise an antihistamine and an H-2 histamine receptor inhibitor. The compositions and methods of this invention have utility in producing anti-inflammatory and cardiovascular activity and for treating shock where low blood pressure is associated with elevated levels of histamine.

In the following co-pending U.S. patent applications:
Ser. No. 80,818 filed Oct. 14, 1970 U.S. Pat. No. 3,759,944;
Ser. No. 80,819 filed Oct. 14, 1970 U.S. Pat. No. 3,736,331;
Ser. No. 330,548 filed Feb. 8, 1973 abandoned;
Ser. No. 310,302 filed Nov. 29, 1972 U.S. Pat. No. 3,868,457;
Ser. No. 80,794 filed Oct. 14, 1970 U.S. Pat. No. 3,734,924;
Ser. No. 335,853 filed Feb. 26, 1973 abandoned;
Ser. No. 306,948 filed Nov. 15, 1972 abandoned;
Ser. No. 312,438 filed Dec. 6, 1972 U.S. Pat. No. 3,808,336;
Ser. No. 230,451 filed Feb. 29, 1972 abandoned;
Ser. No. 290,584 filed Sept. 20, 1972 abandoned;
compounds are described which demonstrate an antagonism to those actions of histamine which are not inhibited by the compounds such as mepyramine which are normally referred to as "antihistamines". The latter compounds have been referred to as H-1 antagonists, and, more recently, we have designated the former as H-2 antagonists (See Black et. al. Nature 1972, 236,385).

Black et. al., cited above, page 390, column 2, state the following:

"Mepyramine has been defined as an H₁-receptor antagonist[1] and burimamide has now been defined as an H₂-receptor antagonits. Used alone, burimamide can antagonize those responses to histamine, such as stimulation of acid gastric secretion, which cannot be blocked by mepyramine; histamine apparently activates H₂-receptors to produce these effects. Histamine responses, such as hypotension which can only be partially antagonized by mepyramine alone can be completely blocked by mepyramine and burimamide given in combination; both H₁ and H₂-receptors seem to be activated by histamine to produce effects of this kind."

Thus, H-1 histamine receptors are those histamine receptors which are inhibited by mepyramine and H-2 histamine receptors are those histamine receptors which are not inhibited by mepyramine but are inhibited by burimamide. For the purpose of the present specification H-2 antagonist compounds described and claimed in our said co-pending applications will be referred to as compounds of class A and the H-1 antagonist compounds such as mepyramine will be referred to as compounds of class B.

The H-2 antagonist compounds of class A comprise the following groups:

a. Thioureas of the general formula I:

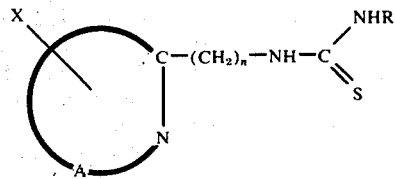

FORMULA I wherein A is such that there is formed together with the carbon and nitrogen atoms shown an unsaturated heterocyclic basic nucleus, preferably having five or six atoms, e.g., imidazole, pyridine, thiazole, or 1,2,4-triazole; X is hydrogen, lower alkyl, halogen or lower alkylthio; n is from 3 to 6; and R is hydrogen, lower alkyl, benzoyl or substituted or unsubstituted phenylethyl.

Particularly preferred compounds of this group are those wherein A is such that, with the carbon and nitrogen atoms shown, it forms an imidazole or thiazole ring. Further preferred features, one or more of which may be present in the compounds of this group are that n should be 4, that X should be hydrogen or a halogen such as bromo and that R should be alkyl (particularly methyl) or hydrogen.

Specific preferred compounds of group (a) are N-methyl-N'-[4-(4(5)-imidazolyl)butyl]thiourea, N-[4-(45)-imidazolyl) butyl]thiourea, N-methyl-N'-[4-(2-thiazolyl)butyl]thiourea and N-methyl-N'-[4-(4-bromo-5-imidazolyl)butyl]thiourea.

b. Compounds of the formula II:

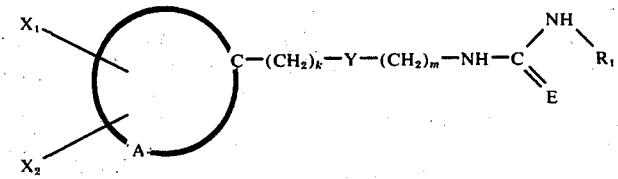

FORMULA II wherein A is such that there is formed together with the carbon atom shown an unsaturated heterocyclic nucleus, which comprises at least one nitrogen atom and may comprise further hetero atoms such as sulphur and oxygen; X₁ is hydrogen, lower alkyl, hydroxyl, trifluoromethyl, benzyl, halogen, amino or

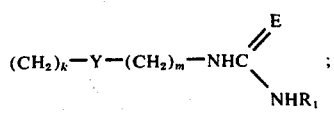

X₂ is hydrogen or, when X₁ is lower alkyl, lower alkyl or halogen; k is 0 to 2 and m is 2 or 3, provided that the sum of k and m is 3 or 4; Y is oxygen, sulphur or NH; E is oxygen, sulphur or NR₂; R₁ is hydrogen, lower alkyl, benzoyl or di-lower alkylamino lower alkyl; and R₂ is hydrogen, nitro or cyano.

Examples of specific unsaturated heterocyclic nuclei are imidazole, pyridine, thiazole, isothiazole, oxazole, isoxazole, pyrazole, triazole, thiadiazole, pyrimidine, pyrazine, pyridazine, benzimidazole or 5,6,7,8-tetrahydro-[1,5-a]pyridine, particularly preferred being imidazole, thiazole, isothiazole and pyridine. Further preferred features, one or more of which may be present in the compounds of this group are that k should be 1 and m should be 2, Y should be sulphur, E should be sulphur or N-cyano, $X_2$ should be hydrogen and $X_1$ should be methyl, hydrogen, bromo, amino or hydroxyl.

Specific preferred compounds of group (b) are N-methyl-N'-[2-((5-methyl-4-imidazolyl)methylthio)ethyl]thiourea, N-methyl-N'-[2-((4-imidazolyl)methylthio)ethyl]thiourea, and N-cyano-N'-methyl-N''-[2-((4-methyl-5-imidazolyl)methylthio)ethyl]guanidine.

c. Amidine derivatives of the formula III:

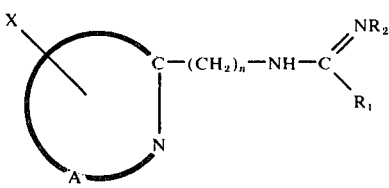

FORMULA III wherein A is such that there is formed together with the carbon and nitrogen atom shown an unsaturated heterocyclic basic nucleus having five or six atoms,; X is hydrogen, hydroxyl, trifluoromethyl, amino, halogen, lower alkyl or lower alkylthio; n is from 2–5; $R_1$ is lower alkyl; phenyl optionally mono-substituted by halogen, hydroxy or nitro; benzyl; lower alkythio-lower alkyl; —NHR₃ or —SR₄; $R_2$ is hydrogen, an alkyl group containing from 1–4 carbon atoms, phenyl, benzyl, or, when $R_1$ is —NHR₃, cyano or nitro; $R_3$ is hydrogen, methyl, benzyl or amino; and $R_4$ is an alkyl group having 1 to 6 carbon atoms, an alkenyl or alkynyl group having 2 to 6 carbon atoms or $(CH_2)_m Z$ where m is 1 to 3 and Z is phenyl optionally mono-substituted by halogen, hydroxy or nitro; hydroxy; di-lower alkylamino; cyano; carboxy; phenoxy; benzhydryloxy; or imidazolyl and wherein $R_3$ or $R_4$ may, with $R_2$, form a five membered ring with the adjacent atoms.

As in the case of group (b) above, examples of specific unsaturated heterocyclic nuclei are imidazole, pyridine, thiazole, isothiazole, oxazole, isoxazole, pyrazole, triazole, thiadiazole, pyrimidine, pyrazine and pyridazine of which imidazole, thiazole, isothiazole and pyridine are particularly preferred. Further preferred features, one or more of which may be present in the compounds of this group are that n should be from 3 to 5, that X should be hydrogen, methyl, bromo, amino or hydroxyl and that $R_1$ should be amino, methylamino or —SR₄.

Specific preferred compounds of group (c) are S-(2-phenoxyethyl)-N-[3-(4-imidazolyl)propyl]isothiourea, S-(p-chlorobenzyl)-N-[3-(4-imidazolyl)propyl]isothiourea, S-ethyl-N-[3-(4-imidazolyl)propyl]isothiourea and 4-(3-guanidinopropyl)imidazole d. Isothioureas of the formula IV:

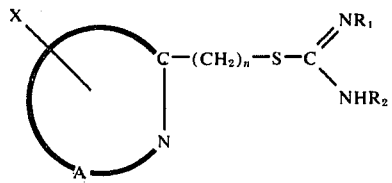

FORMULA IV wherein n is from 2 to 4; A is such that it forms with the carbon and nitrogen atom shown an unsaturated heterocyclic basic nucleus having five or six atoms; $R_1$ is hydrogen or lower alkyl; $R_2$ is hydrogen, lower alkyl, amino or benzyl or $R_1$ and $R_2$ together form an ethylene bridge; and X is hydrogen, halogen or benzyl.

In the preferred compounds of group (d) the unsaturated heterocyclic nucleus is imidazole, pyridine, pyrazole or triazole and further preferred features, one or more of which may be present in the compounds of this group are that X should be hydrogen and that $R_1$ and $R_2$ should be hydrogen or methyl.

Specific preferred compounds of group (d) are: $N_1 N'$-dimethyl-S-[2-(4(5)-imidazolyl)ethyl]isothiourea and S-[4-(4(5)-imidazolyl)butyl]isothiourea.

e. Amidines of the formula V.

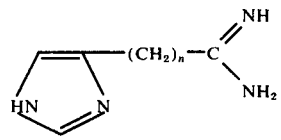

FORMULA V wherein n is 3 or 4.

f. The pharmaceutically acceptable acid addition salts of all the compounds set out in groups (a) to (e) above.

A particular group of guanidine compounds which are H-2antagonists of class A and which are the H-2 histamine receptor inhibitors of the pharmaceutical compositions and methods of the present application consits of 4-(3-guanidinopropyl)-imidazole and a compound represented by formula II above wherein A is such that there is formed together with the carbon atom shown an imidazole, thiazole, isothiazole or pyridine ring; $X_1$ is hydrogen, lower alkyl, halogen, amino or hydroxyl; $X_2$ is hydrogen; k is 1; m is 2; E is NR₂; $R_1$ is hydrogen or lower alkyl and $R_2$ is hydrogen, nitro or cyano, or a pharmaceutically acceptable acid addition salt thereof.

The compounds of class B comprise all those compounds generally recognised and known as antihistamines, all of which compounds therefore antagonise histamine H-1 receptors. The preferred compounds of class B are those which have the minimal sedating affect on the central nervous system and the duration of whose effect is of the same order as that of the class A compound with which it is included in the composition of this invention. Such preferred compounds include mapyramine, mebrophenhydramine, promethazine, diphenhydramine, chlorpheniramine, triprolidene, antazoline, bromodiphenydramine, parabromdylamine, carbinoxamine, cyproheptadine, chlorcyclizine, dimethindene, diphenylpyraline, dimethothiazine methdilazine, trimeprazine, mebhydroline, methapyrilene, phenindamine, pheniramine, phenyltoloxamine and pyrrobutamine.

The compounds of class B which are found to be particularly suitable are mepyramine, mebrophenhydramine and promethazine.

According to the present invention we provide a pharmaceutical composition which comprises a compound of class A and a compound of class B together with a pharmaceutically acceptable diluent or carrier.

The compounds of class A may be prepared by methods which are described in the co-pending applications listed hereabove. These methods are described as follows:

Thus, a suitable method for the production of compounds of group (a) involves the treatment of an amine of formula VI:

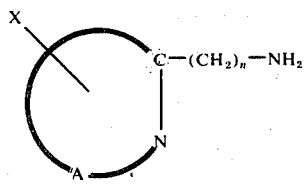

FORMULA VI wherein A, X and n have the same significance as in formula I with an isothiocyanate of formula R'N=C=S wherein R' is lower alkyl or substituted or unsubstituted aroyl or aralkyl followed in the case where R' is benzoyl by hydrolysis to the compound of formula I wherein R is hydrogen.

The starting material for the production of compounds of group (b) is a compound of formula VII:

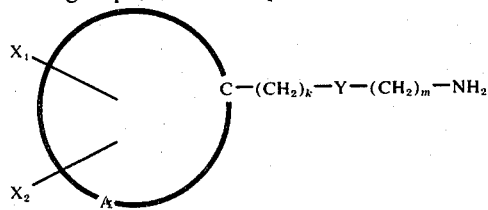

FORMULA VII wherein $X_1$, $X_2$, A, k, m and Y have the same significance as in formula II. This substance is reacted with a compound of the formula VIII:

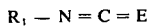

FORMULA VIII wherein $R_1$ has the same significance as in formula II and E is sulphur or oxygen or with a compound of the formula IX:

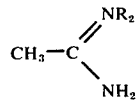

wherein $R_2$ has the same significance as in formula II.

The compounds of group (c) may be produced from the amine of formula VI wherein A, X and n have the same significance as in formula III. Reaction thereof with a compound of formula X or of formula XI:

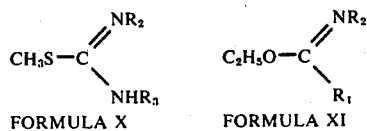

FORMULA X     FORMULA XI wherein $R_2$ and $R_3$ have the same significance as in formula III and $R_1$ is lower alkyl, substituted or unsubstituted phenyl, aralkyl or alkylthioalkyl yields respectively products of formula III wherein $R_1$ is $NHR_3$ or is lower alkyl, substituted or unsubstituted phenyl, aralkyl or alkylthioalkyl. To produce compounds of formula III wherein $R_1$ is $SR_4$, the amine of formula VI is first converted to the thiourea of formula I wherein X, A and n have the same significance as in formula III and R has the same significance as $R_2$ in formula III and this thiourea is then reacted with a compound of formula XII:

FORMULA XII wherein $R_4$ has the same significance as in formula III and Y is halogen or hydroxy.

The compounds of group (d) may be formed from a substance of the formula XIII:

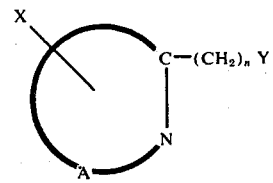

FORMULA XIII wherein A, X and n have the same significance as in formula IV and Y is hydroxy or halogen by treatment thereof with a thiourea of formula XIV:

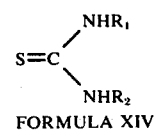

FORMULA XIV wherein $R_1$ and $R_2$ have the same significance as in formula IV.

Finally, the compounds of group (e) can be prepared from a nitrile of formula XV:

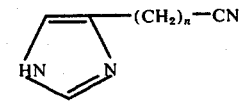

FORMULA XV wherein n is 3 or 4 by reaction thereof with methanol or ethanol to give an imino - ether of formula XVI:

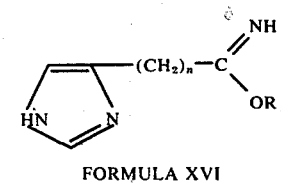

FORMULA XVI wherein $n$ is 3 or 4 and R is methyl or ethyl which on treatment with ammonia yields the required compound of formula V.

The preferred compounds of class B are, as stated above, all well known and readily available antihistamine compounds.

The acute anti-inflammatory action of the compositions according to the present invention may be demonstrated by means of the biological screening tests which are commonly employed for this purpose. One such screening test is the rat paw oedema test wherein the swelling of a rat's paw caused by the injection of certain substances such as histamine, the histamine-releasing agents known as compound 48/80 and 5-HT, yeast, kaolin and carageenin into the plantar surface is measured (e.g. plethysmographically) both in untreated control rats and in rats which have been treated sub-cutaneously with the anti-inflammatory composition. Another such test is the guinea-pig U-V erythema test wherein the depilated skin of a guinea-pig is exposed for a standard time to U.V. radiation and the intensity of the resultant erythema in control and treated animals is assessed over a period of hours.

The compositions according to the invention have been assessed on both these tests and, as will be apparent from the experimental data hereinafter, have shown marked anti-inflammatory ction at doses containing about action micromoles per kilogram of the H-2 antagonist of class A and from about 50 to 100 micromoles per kilogram of the antihistamine of class B. These doses were given by sub-cutaneous injection. It will be noted, where individual compounds of class A and class B have been also tested separately, that the anti-inflammatory action shown by each compound alone is much less than that shown by the combination.

The cardiovascular activity of the compositions according to the present invention has been assessed in anaesthetised cats, dogs and rabbits. In the anaesthetised cat or dog, histamine has long been known to cause hypotension. When administered intravenously in relatively large doses (e.g., greater than 0.02 micromoles/Kg.), this effect has been found to be refractory to treatment with the H-1 antagonist compounds of class B (Folkow et al., Acta Physiol. Scand. 1948, 15 264). We have found that the H-2 antagonist compounds of Class A have no inhibiting influence on this effect but we have now found that the compositions of the present invention containing from 5 to 100 micromoles per kilogram of the H-2 antagonist of class A and from 10 to 50 micromoles per kilogram of the antihistamine of class B, given intravenously, can completely inhibit this histamine-induced hypotension. In the anaesthetised rabbit, intravenously administered histamine may produce pressor, depressor or biphasic changes in blood pressure depending on the dose and the anaesthetic used. The H-1 antagonist compounds of class B are known to reverse the pressor responses to depressor responses (see Staub, Ann. Inst. Pasteur, 1939, 63 400) and we have shown that the H-2 antagonist compounds of class A potentiate the pressor responses. The compositions of our invention containing from 1 to 50 micromoles per kilogram of the H-2 antagonist of class A and from 1 to 10 micromoles per kilogram of the antihistamine of class B, given intravenously, completely abolished both pressor and depressor responses.

The compositions of the present invention also have utility in antagonising other pharmacological actions where both H-1 and H-2 histamine receptors are involved. Thus they can be useful in combating the effects of certain types of shock, for example, the shock-like state produced by bacterial endotoxins. By a mechanism which is thought to involve histamine, these endotoxins, which are polysaccharide-protein-lipid complexes released on bacterial disintegration, cause a profound fall in arterial blood pressure. Anaesthetised rats, which had previously been treated with the compositions of our invention containing from 10 to 100 micromoles per kilogram of the antihistamine and from 100 to 1000 micromoles per kilogram of the H-2 antagonist, when given intravenously 5 mg./Kg. of such an endotoxin showed a significantly smaller fall in blood pressure than untreated control rats.

The compositions of the present invention, in addition to the active compounds of class A and class B, comprise a pharmaceutically acceptable carrier. Advantageously the compositions will be made up in a dosage unit form appropriate to the desired mode of administration. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Other pharmacologically active compounds may in certain cases be included in the pharmaceutical compositions.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredients will be present in the composition in an effective amount to inhibit both H-1 and H-2 histamine receptors. The route of administering may be orally, topically or may be parenterally e.g., sub-cutaneously or intravenously.

Preferably, each dosage unit will contain the active ingredients of class A (H-2 antagonist) in an amount of from about 50 mg to about 500 mg and the active ingredient of class B (antihistamine) in an amount of from about 30 mg. to about 250 mg.

The active ingredients will preferably be administered in equal doses three to six times per day. The daily dosage regimen will preferably be from about 500 mg to about 3000 mg.

For therapeutic use, the pharmacologically active compounds in the pharmaceutical composition of our invention will normally be administered in the basic form or in the form of an addition salt with a pharmaceutically acceptable acid. Such addition salts include those with hydrochloric, hydrobromic, hydriodic, sulphuric, picric and maleic acids.

Advantageously the composition will be made up in a dosage form appropriate to the desired mode of administration, for example as a tablet, capsule, injectable solution or as a cream or ointment for topical administration.

The invention is illustrated but in no way limited by the following examples.

EXAMPLE 1

40 rats were used for the tests described in this Example. Divided into four groups of 10 rats each, the rats were given a subcutaneous injection of 0.3 ml/100 g. body weight of the solutions containing the following:

| | |
|---|---|
| Group 1 (Control) | : Saline |
| Group 2 (Antihistamine) | : 63 micromoles/Kg. of mepyramine |
| Group 3 (H-2 Antagonist) | : 500 micromoles/Kg. of N-methyl-N'-[4(5)-imidazolyl)-butyl]thiourea |
| Group 4 (Combination) | : 63 micromoles/Kg. of mepyramine plus 500 micromoles/Kg. of N-methyl-N'-[-4(5)-imidazolyl)butyl]thiourea. |

30 minutes after this injection the plantar surface of a paw of each rat was injected with 0.2 ml. of a solution containing 4 micrograms of histamine as irritant. The average change in paw colume (expressed as a volume-time integral over 4 hours) was assessed plethysmographically for each roup and is shown in Table 1. The values obtained for each of groups 2, 3 and 4 expressed as a percentage of that obtained for group 1, are also shown.

TABLE 1

| Group No. | Average Paw Volume Change | Percentage of Group 1 |
|---|---|---|
| 1 | 0.70 ± 0.14 | 100 |
| 2 | 0.08 ± 0.17 | 11 |
| 3 | 0.30 ± 0.19 | 43 |
| 4 | −0.45 ± 0.14 | 0 |

The negative figure obtained from group 4 is due to the fact that, not only was no swelling caused by the histamine irritant but the paw volume actually reduced due to the absorption during the time of the test of the originally injected vehicle.

EXAMPLES 2 to 6

The experiment described in Example 1 was repeated using, in place of histamine, the irritants as shown in table 2.

In each case it can be seen that the amount of swelling of the paw of the rats in group 4 is very considerably less than that in the case of the rats in group 2 or group 3.

EXAMPLE 7 to 22

The procedure of Example 2 (i.e. using 100 micrograms of 48/80 as irritant) was repeated using a two groups of 10 rats corresponding to group 1 and 4 in Examples 1 to 6. Thus one group of 10 rats were given a subcutaneous injection of 0.3 ml/100 g. body weight of saline and a second group of 10 rats was administered a subcutaneous injection of 0.3 ml/100 g. body weight of a solution containing 88 micromoles/Kg. of mepyramine and 500 micromoles/Kg. of an H-2 antagonist as shown in Table 3. The average change in paw volume in the rats of the second group expressed, as in Example 1 to 6, as a percentage of the

TABLE 2

| Example No | 2 | | 3 | | 4 | | 5 | | 6 | |
|---|---|---|---|---|---|---|---|---|---|---|
| Irritant | 48/80 | | 5/HT | | Yeast | | Kaolin | | Carageenin | |
| Amount of Irritant Used/ Vol. Injected | 100 micrograms in 0.2 ml. | | 25 micrograms in 0.1 ml. | | 250 micrograms in 0.2 ml. | | 50 micrograms in 0.1 ml. | | 20 micrograms in 0.1 ml. | |
| | Av. Vol. Change | % age | Av. Vol. Change | % age | Av. Vol. Change | % age | Av. Vol. Change | % age | Av. Vol. Change | % age |
| Group 1 | 3.10 ± 0.20 | 100 | 2.35 ± 0.22 | 100 | 2.55 ± 0.15 | 100 | 1.65 ± 0.25 | 100 | 1.85 ± 0.28 | 100 |
| Group 2 | 2.70 ± 0.35 | 87 | 1.80 ± 0.20 | 76 | 1.65 ± 0.15 | 65 | 0.95 ± 0.17 | 58 | 1.45 ± 0.20 | 78 |
| Group 3 | 2.80 ± 0.25 | 90 | 1.50 ± 0.20 | 64 | 1.70 ± 0.20 | 67 | 1.26 ± 0.17 | 76 | 1.85 ± 0.28 | 100 |
| Group 4 | 0.90 ± 0.20 | 29 | 0.15 ± 0.12 | 6 | 0.80 ± 0.15 | 31 | 0.65 ± 0.15 | 39 | 0.85 ± 0.19 | 46 |

TABLE 3

| Example No. | H - 2 Antagonist Used |
|---|---|
| 7 | N-[4-(4-imidazolyl)butyl]thiourea |
| 8 | N-methyl-N'-[4-(2-thiazolyl)butyl]thiourea |
| 9 | N-methyl N'-[4-(4-bromo-5-imidazolyl)butyl]-thiourea |
| 10 | N-methyl-N'-[5-(4-imidazolyl)pentyl]thiourea |
| 11 | N-methyl-N'-[3-(4-imidazolyl)propyl]thiourea |
| 12 | N-isopropyl-N'-[4-(4-imidazolyl)butyl]thiourea |
| 13 | N-methyl-N'-[4-(3-(1,2,4)-triazolyl)butyl]-thiourea |
| 14 | N-methyl-N'-[2-((4-methyl-5-imidazolyl)-methylthio)ethyl]thiourea |
| 15 | N-methyl-N'-[2-(4-imidazolylmethylthio) ethyl]-thiourea |
| 16 | N-cyano-N'-methyl-N''-[2-((4-methyl-5-imidazolyl)-methylthio)ethyl]guanidine |
| 17 | N-methyl-N'-[3-(4-imidazolylmethylthio)-propyl]thiourea |
| 18 | N-methyl-N'-[2-((4-isopropyl-5-imidazolyl)-methylthio) ethyl]thiourea. |
| 19 | S-(2-phenoxyethyl)-N-3-(4-imidazolyl)-propyl isothiourea |
| 20 | S-(p-chlorobenzyl)-N-[3-(4-imidazolyl) propyl]-isothiourea |
| 21 | S-ethyl-N-[3-(4-imidazolyl)propyl]isothiourea |
| 22 | 4-(3-guanidinopropyl)-imidazole | change observed in the control group lay within the range of from 15% to 70%.

EXAMPLE 23

The procedure of Examples 7 to 22 was repeated using, as H-2 antagonist 500 micromoles/Kg. of the following compounds:

a. N,N'-dimethyl-S-[2-(4(5)-imidazolyl)ethyl]isothiourea
b. S-[4-(4(5)-imidazolyl)butyl]isothiourea
c. 5- (4(5)-imidazolyl)valeramidine
d. N-methyl-N'-[4-(2-pyridyl)butyl]thiourea
e. N-methyl-N'-[2-((3-pyridazinyl)methylthio)ethyl]-thiourea
f. N-methyl-N'-[2-((3-hydroxy-2-pyridyl)methylthio)-ethyl]thiourea
g. N-methyl-N'-[2-((5-(2-amino-1,3,4-thiadiazolyl)-methylthio)ethyl]thiourea.
h. N-methyl-N'-[3-(2-oxazolyl)thiopropyl]thiourea
i. N-methyl-N'-[2-(4-imidazolylmethoxy)ethyl]thiourea
j. N-methyl-N'-[3-(2-pyridylamino)propyl]thiourea
k. N-methyl-N'-[2-((4-methyl-5-imidazolyl)methylthio)-ethyl]urea
l. 2-[(4-imidazolyl)methylthio]ethylguanidine
m. N-(2-[(4-methyl-5-imidazolyl)methylthio]ethyl)-N'-nitroguanidine
n. N-methyl-N'-[2-(4-trifluoromethyl-5-imidazolyl)-methylthio) ethyl]thiourea
o. N-methyl-N'-[2-(2-pyrimidyl)methylthio)ethyl]-thiourea
p. N-methyl-N'-[2-(2-pyrazinyl)methylthio)ethyl]-thiourea
q. N-methyl-N'-[2-(4-bromo-3-isothiazolyl)methylthio)-ethyl]thiourea.

In each case the average swelling of the rat's paw in the second group was very much less than in the case of the control group.

EXAMPLES 24 and 25

The procedure of Examples 7 to 21 was repeated, the second group of 10 rats being administered subcutaneously 0.3 ml/100 g. body weight of a solution containing 500 micromoles/Kg. of N-methyl-N'-[4-(4(5)-imidazolyl)butyl] thiourea and an antihistamine as shown in Table 4. The table also shows the average paw volume change expressed as a percentage of the control group.

TABLE 4

| Example No. | Antihistamine Used | Amount of Antihistamine | % age |
|---|---|---|---|
| 24 | Promethazine | 88 micromoles/Kg. | 0.6 |
| 25 | Mebrophenhydramine | 72 micromoles/Kg. | 0.0 |

EXAMPLE 26

The procedure of Examples 24 and 25 was repeated using as antihistamine from 50 to 100 micromoles/Kg. of the following substances: diphenhydramine, chlorpheniramine, triprolidene, antazoline, bromodiphenhydramine, parabromdylamine, carbinoxamine, cyproheptadine, chlorcyclizine, dimethindene, diphenylpyraline, dimethothiazine, methdilazine, trimeprazine, mebhydroline, methapyrilene, phenindamine, pheniramine, phenyltoloxamine and pyrrobutamine. In each case the average swelling of rats paw in the second group was very much less than in the case of the control group.

EXAMPLE 27

Four groups each of 7 guinea-pigs were injected subcutaneously with compositions corresponding to those given to rats in groups 1 - 4 in experiments 1 to 6. Thirty minutes later three 0.5 cm. diameter circles on the depilated skins of the guinea-pigs were irradiated for 1 minute with a Hanovia U.V. lamp and the intensity of the resultant areas of erythema were scored after 2 and 5 hours.

The scoring system used was to assign 0, ½ or 1 to each irradiated circle according to the intensity of erythema; for each animal, fully developed erythema in each circle would give a maximum score of 3 and the maximum score for each group of 7 animals would be 21. Assessments were made by two investigators who scored the results independently on a completely "blind" basis. Analysis of variance showed that there was no significant differences between observers and their scores have been averaged as shown in Table 5.

TABLE 5

| Treatment | Hours | |
|---|---|---|
| | 2 | 5 |
| Group 1 | 16 | 17 |
| Group 2 | 6 | 15 |
| Group 3 | 5 | 7 |
| Group 4 | 1.5 | 4 |
| ANALYSIS OF VARIANCE | | |
| F and p | | |
| Group 2 | 36.39 | 3.95 |
| | 0.001 | N.S. |
| Group 3 | 47.76 | 64.43 |
| | 0.001 | 0.001 |
| Group 4 | 7.5 | 0.22 |
| | 0.01 | N.S. |

EXAMPLE 28

To cats, anaesthetised with an intravenously administered dose of 100 mg/Kg. of chloralose, was intravenousl given doses of histamine in the range of 0.01 to 0.10 micromoles/Kg. of histamine. The resultant vasodilation and hypotension was not affected by an intravenous dose of 35 micromoles/Kg. of mepyramine but a subsequent intravenous infusion of N-methyl-N'-[4-(4(5)-imidazolyl)-butyl] thiourea at a rate of 3 micromoles/Kg./minute over 30 minutes completely abolished the hypotension.

EXAMPLE 29

The experiment of Example 28 was repeated in dogs which had been anaesthetised with an intravenously administered dose of 30 mg./Kg. of nembutal. The hypotension was again abolished.

In the case of both Example 28 and 29, the abolition of histamine-induced hypotension could be equally well achieved by a single intravenous dose of a composition comprising 35 micromoles/Kg. of mepyramine and 90 micromoles/Kg. of N-methyl-N'-[4-(4(5)-imidazolyl)butyl]-thiourea.

EXAMPLE 30

The experiments of Examples 28 and 29 were repeated using, as H-2 antagonist 9 micromoles/Kg. of N-methyl-N'-[2-((4-methyl-5-imidazolyl)methylthio)ethyl]thiourea administered intravenously either in a composition also comprising 35 micromoles/Kg. of mepyramine or subsequently to the mepyramine as an infusion over 30 minutes.

EXAMPLE 31

The experiments of Examples 28 and 29 were repeated using, as antihistamine (a) 18 micromoles/Kg. of promethazine and (b) 14 micromoles/Kg. of mebrophenhydramine. In each case the hypotension was abolished.

EXAMPLE 32

To rabbits, anaesthetised with an intraperitoneally administered mixture of 700 mg/Kg. of urethane and 40 mg/Kg. of pentobarbitone, histamine in the dose range 0.0625 to 0.50 micromoles/Kg. was given intravenously and produced pressor responses. An intravenous dose of 3.5 micromoles/Kg. of mepyramine reversed this pressor response to a depressor response whereas an intravenous dose of 1 micromole/Kg./minute of N-methyl-N'-[4-(4(5)-imidazolyl)butyl]thiourea over 30 minutes potentiated the histamine-induced pressor response. However, the intravenous administration of a solution comprising both 3.5 micromoles/Kg. of mepyramine and 30 micromoles/Kg. of N-methyl-N'-[4(4(5)-imidazolyl)-butyl]thiourea completely abolished the histamine-induced pressor response.

EXAMPLE 33

When the experiments of Examples 28, 29 or 32 are repeated using, as H-2 antagonist any of the substances set out in Examples 7 to 14 and 16 to 23 in conjunction with mepyramine as antihistamine, the histamine-induced cardiovascular effects are abolished in each case.

EXAMPLE 34

When the experiments of Examples 28, 29 or 32 are repeated using N-methyl-N'-[4-(4(5)-imidazolyl)-butyl]thiourea as H-2 antagonist and any of the substances listed in Example 26 as anti-histamine, the histamine-induced cardiovascular effects are abolished in each case.

EXAMPLE 35

A group of seven rats were anaesthetised by intraperitoneal injection of 60 mg./Kg. of pentobarbitone sodium, under which conditions their blood pressure was of the order of 110 mm.Hg. Intravenous infusion of saline at a rate of 1 ml/hour was commenced and, after 30 minutes an intravenous injection of 5 mg./Kg. of lipopolysaccharide B derived from S. enteritidis was given. Within a short period (about 10-15 minutes) the blood pressure had fallen to an average minimum level of 23 mm. Hg. A second group of seven rats similarly treated but in this case the intravenous infusion was of a composition according to the present invention comprising a solution of promethazine and N-methyl-N'-[2-((5-methyl-4-imidazolyl)methylthio)-ethyl]thiourea in a molar weight ratio of 1:10. This solution was administered at a rate such that, over the 30 minutes prior to the intravenous injection of the endotoxin, 60 micromoles/Kg. rat body weight of mepyramine and 600 micromoles/Kg. rat body weight of N-methyl-N'-[2-((5-methyl-4-imidazolyl)methylthio)ethyl]-thiourea had been given. The average minimum blood pressure which again was measured after 10-15 minutes from the injection of the endotoxin was in this case 37 mm.Hg.

EXAMPLE 36

When the experiment of Example 35 is repeated using as the composition of our invention any one of the H-2 antagonist substances set out in Examples 1,7–13 and 15 to 23 in conjunction with any one of the antihistamine listed in Example 26, mapyramine or mebrophenhydramine, similar results are obtained.

EXAMPLE 37

| Ingredients | Amounts |
| --- | --- |
| N-methyl-N'-[4-(4(5)-imidazolyl)-butyl]thiourea | 250 mg. |
| mepyramine | 120 mg. |
| sucrose | 100 mg. |
| starch | 20 mg. |
| talc | 7 mg. |
| stearic acid | 3 mg. |

The ingredients are screened, mixed and filled into a hard gelatin capsule.

EXAMPLE 38

| Ingredients | Amounts |
| --- | --- |
| N-methyl-N'-[2-((5 methyl-4-imidazolyl)methylthio)ethyl]-thiourea | 200 mg. |
| mebrophenhydramine | 150 mg. |
| lactose | 150 mg. |

The ingredients are screened, mixed and filled into a hard gelatine capsule.

EXAMPLE 39

| Ingredients | Amounts |
| --- | --- |
| N-methyl-N'-[4-(4(5)-imidazolyl)-butyl]thiourea | 100 mg. |
| Promethazine | 50 mg. |

The ingredients are dissolved in distilled water and packaged into sealed ampoules.

The compositions prepared as in Examples 37 to 39 are administered to a subject within the dose ranges given hereabove to produce anti-inflammatory activity.

EXAMPLE 40

Preparation of S-[2-(4(5)-imidazolyl)ethyl]isothiourea dihydrobromide

A solution of 4(5)-(2-hydroxyethyl)imidazole (6.0 g.) and thiourea (4.1 g.) in 48% aqueous hydrobromic acid (37 ml.) is heated under reflux for 17 hours. Following evaporation to dryness, the solid residue is recrystallized from isopropyl alcohol-ethanol-ether, yielding S-[2-(4(5)-imidazolyl)ethyl]-isothiourea dihydrobromide, m.p. 208°–212° C. Recrystallization from the same solvents yields pure product, m.p. 210°–212° C.

EXAMPLE 41

Preparation of N,N'-dimethyl-S-[2-(4(5)-imidazolyl)ethyl]-isothiourea dihydrobromide A mixture of 4(5)-(2-hydroxyethyl)imidazole (2.24 g.), N,N'-dimethylthiourea (2.04 g.) and 48% aqueous hydrobromic acid (12 ml.) is caused to react in a manner similar to that described in Example 40. The pure product m.p. 203°–204° C., is obtained by recrystallization from absolute alcohol.

EXAMPLE 42

Preparation of S-[4-(4(5)-imidazolyl)butyl]isothiourea dihydrobromide

4-[4(5)-Imidazolyl]butyric acid hydrochloride (72.0 g.) is esterified using a solution of gaseous hydrogen chloride in ethanol (14.5%). The solution is heated under reflux for 18 hours in the presence of a molecular sieve contained in a Soxhlet apparatus. Concentration affords the ethyl ester hydrochloride (78.2 g.) which is converted into the base by dissolving in absolute alcohol (200 mg.) and neutralizing with a solution prepared from sodium (7.93 g.) in alcohol (250 ml.). Following removal of inorganic material the crude ester base (54.7 g.) is isolated and used without further purification. This ester is dissolved in anhydrous tetrahydrofuran (700 ml.) and added slowly to a stirred suspension of lithium aluminium hydride (46.6 g.) in anhydrous tetrahydrofuran (220 ml.). Stirring is continued at room temperature for 17 hours, whereupon water (84 ml.) is slowly added, followed by the application of moderate heat for 15 minutes. The solid present is removed by filtration and extracted three times with hot tetrahydrofuran. The combined extracts are evaporated, affording 4(5)-(4-hydroxybutyl)imidazole (23 g.), a sample of which is converted into an oxalate salt, m.p. 104°–106° C.

A mixture of 4(5)-(4-hydroxybutyl)imidazole (2.24 g.), thiourea (1.22 g.) and 48% aqueous hydrobromic acid (10 ml.) is caused to react in a manner similar to that described in Example 40. The initial product obtained (m.p. 110°–115° C.) is recrystallized from methanol-nitromethane-ethyl acetate affording S-[4-(4(5)-imidazolyl)butyl]isothiourea dihydrobromide in three crops:

1.1 g. m.p. 113°–114° C.; 0.4 g. m.p. 109°–113° C.; 0.6 g. m.p. 110°–112° C.

EXAMPLE 43

Preparation of S-ethyl-N-[3-(4(5)-imidazolyl)propyl]isothiourea dihydriodide and sulphate Ethyl iodide (12.5 g.) is added to a solution of N-[3-(4(5)-imidazolyl)propyl]thiourea hydriodide (23.0 g.) in absolute ethanol (250 ml.) containing water (2 ml.). The resultant solution is heated under reflux for four hours and concentrated under reduced pressure. Recrystallization of the residue from ethanol-ether yields S-ethyl-N-[3-(4(5)-imidazolyl)-propyl]isothiourea dihydriodide, m.p. 113°–114° C.

A solution of S-ethyl-N-[3-(4(5)-imidazolyl)propyl]-isothiourea dihydriodide (20 g.) in water is passed down an ion-exchange column ($SO_4^{--}$ form, 250 ml.). Following elution with water, the eluate is concentrated under reduced pressure. Recrystallization of the residue from water-isopropyl alcohol yields S-ethyl-N-[3-(4(5)-imidazolyl)propyl]isothiouronium sulphate, m.p. 184°–186° C.

EXAMPLE 44

Preparation of S-(p-chlorobenzyl)-N-[3-(4(5)-imidazolyl)propyl]-isothiourea dihydrochloride The solution obtained from the addition of p-chlorobenzyl chloride (1.3 g.) to N-[3-(4(5)-imidazolyl)-propyl]thiourea (1.5 g.) in 2N hydrochloric acid (25 ml.) containing acetone (15 ml.) is heated under reflux for 2.5 hours. Concentration followed by recrystallization from ethanol-isopropyl alcohol affords S-(p-chlorobenzyl)-N-[3-(4(5)-imidazolyl)propyl]-isothiourea dihydrochloride, m.p. 217°–219° C.

EXAMPLE 45

Preparation of S-(2-phenoxyethyl)-N-[3-(4(5)-imidazolyl)propyl]-isothiourea dihydrobromide The solution obtained from the addition of 2-phenoxyethyl bromide (2.0 g.) to N-[3-(4(5)-imidazolyl)-propyl]-thiourea hydrobromide (2.6.) in absolute ethanol (30 ml.) containing water (1 ml.) is heated under reflux for 48 hours. Concentration followed by recrystallization from isopropyl alcohol-ether affords S-(2-phenoxyethyl)-N-[3-(4(5)-imidazolyl)propyl]isothiourea dihydrobromide, m.p. 153°–156° C.

EXAMPLE 46

Preparation of 3-(4(5)-imidazolyl)propylguanidine sulphate

Pure 4(5)-(3-aminopropyl)imidazole (10.5 g) is added to a solutin of S-methylthiouronium sulphate (11.8 g) in water (125 ml). The resultant solution is refluxed for four hours, cooled and the acidified with the minimum quantity of sulphuric acid. Following concentration to low volume, ethanol is added which results in the separation of a colourless solid. This is filtered off, and twice recrystallized from water-methanol giving pure 3-(4(5)-imidazolyl)propylguanidine sulphate, m.p. 288°–290° C.

EXAMPLE 47

Preparatin of N-[3-(4(5)-imidazolyl)propyl]acetamidine dihydrochloride

4(5)-(2-Chloroethyl)imidazole hydrochloride (200 g.) is dissolved in dimethylformamide (600 ml.) and the solution treated with charcoal and filtered. The filtrate is added gradually to a stirred suspension of sodium cyanide (176 g.) in dimethylformamide (2.25 l.) maintained at 130°–135° C. The addition requires 35 minutes and after this time the temperature is maintained at 135° C. for five minutes. After cooling in an ice bath to 10° C., suspended solid is removed by filtration and washed with dimethylformamide. The filtrate is concentrated under reduced pressure and final traces of dimethylformamide are removed with p-xylene (2×200 ml). The dry residue is dissolved in distilled water (500 ml.) and charged into a one liter extractor (volume including washings now 750 ml.) and extracted continuously with isopropyl acetate. The extracts are dried over magnesium sulphate, treated with charcoal and concentrated to low bulk. Cooling affords 4(5)-(2-cyanoethyl)imidazole, m.p. 71°–74° C.

Alternative conditions for the synthesis of 4(5)-(2-cyanoethyl)imidazole are as follows: a solution of 4(5)-

(2-chloroethyl)imidazole hydrochloride (136 g.) in water (500 ml.) is added, with stirring to a solution of sodium cyanide (420 g.) in water (1.65 l.). The resultant mixture is heated at 60°–65° C. for 20 hours. After cooling, the solution is treated with charcoal, filtered and concentrated under reduced pressure. The dry residue is extracted with hot ethyl acetate (5. l.) and the extracts are treated with charcoal and concentrated under reduced pressure, affording 4(5)-(2-cyanoethyl)-imidazole, m.p. 70°–71° C. A pure sample of the base, m.p. 71°–73° C., is obtained by recrystallization from isopropyl acetate. A sample of the hydrochloride, m.p. 118°–120° C., is obtained by acidification with dry hydrogen chloride in ether.

A solution of 4(5)-(2-cyanoethyl)imidazole (61 g.) in absolute alcohol (600 ml.) is saturated with gaseous ammonia at −20° C. The resultant solution is hydrogenated over Raney nickel catalyst (approximately 4 g.) at 100 atmospheres pressure for four hours at a temperature of 135°–145° C. After cooling, filtration and treatment with charcoal, the solution is concentrated under reduced pressure, affording 4(5)-3-aminopropylimidazole as a low melting solid. For purification, the amine (61 g.) is dissolved in a solution of sodium bicarbonate (82 g.) in water (1.6 l.) and N-carbethoxyphthalimide (122 g.) added over 0.5 hours. After stirring for 1.5 hours, the solid is collected, washed with water and dried. Recrystallization from aqueous ethanol yields 4(5)-(3-phthalimidopropyl-)imidazole. A pure sample obtained by further recrystallization from aqueous ethanol has m.p. 160°–162° C.

Hydrolysis with 5N hydrochloric acid for 16 hours followed by removal of phthalic acid yields 4(5)-3-aminopropyl-imidazole dihydrochloride, m.p. 156°–158° C. (from ethanol-ether). Treatment with sodium ethoxide in ethanol yields pure 4(5)-(3-aminopropyl)imidazole.

Ethyl acetimidate hydrochloride (3.95 g.) is added rapidly to a mixture of di-n-butyl ether (25 ml.) and a solution of potassium carbonate (4.4 g.) in water (15 ml.). After shaking briefly, the organic layer is separated, dried over sodium sulphate and filtered. A solution of 4(5)-(3-aminopropyl)imidazole (2.0 g.) in dry ethanol (25 ml.) is added to the filtrate and the resultant solution is allowed to stand at room temperature for seven days. The solution is then filtered, concentrated and acidified with ethanolic hydrogen chloride to give a hygroscopic solid. Recrystallization from ethanol-ether with filtration in a dry atmosphere affords N-[3-(4(5)-imidazolyl)propyl]acetamidine dihydrochloride, m.p. 122°–128° C.

EXAMPLE 48

Preparation of 5-(4(5)-imidazolyl)valeramidine dihydrochloride

4-[4(5)-imidazolyl]butyric acid hydrochloride (72.0 g.) is esterified using a solution of gaseous hydrogen chloride in ethanol (14.5%). The solution is heated under reflux for 18 hours in the presence of a molecular sieve contained in a Soxhlet apparatus. Concentration affords the ethyl ester hydrochloride (78.2 g) which is converted into the base by dissolving in absolute alcohol (200 ml) and neutralizing with a solution prepared from sodium (7.93 g) in alcohol (250 ml). Following removal of inorganic material the crude ester base (54.7 g.) is isolated and used without further purification.

This ester is dissolved in anhydrous tetrahydrofuran (700 ml) and added slowly to a stirred suspension of lithium aluminium hydride (46.6 g.) in anhydrous tetrahydrofuran (220 ml.). Stirring is continued at room temperature for 17 hours whereupon water (84 ml) is slowly added, followed by the application of moderate heat for 15 minutes. The solid present is removed by filtration and extracted three times with hot tetrahydrofuran. The combined extracts are evaporated to an oil (23 g) a sample of which is converted into an oxalate salt, m.p. 104°–106° C. for characterisation.

The foregoing 4(5)-(4-hydroxybutyl)imidazole (10 g) is added slowly to thionyl chloride (20 ml) with stirring. The resultant solution is heated on the steam bath for ten minutes and evaporated to an oil which is re-evaporated with benzene to remove last traces of thionyl chloride. The residual oil is dissolved in alcohol, treated with charcoal, concentrated and diluted with ether. Cooling affords 4(5)-(4-chlorobutyl)imidazole hydrochloride as a stickly solid (12 g). Without further purification, the chloro compound (10.0 g) is dissolved in anhydrous dimethylformamide (43 ml) and slowly added to a dispersion of sodium cyanide (8.3 g) in anhydrous dimethylformamide (330 ml) at 110° C., with stirring. After addition, the mixture is maintained at 110° C. for 15 minutes and then concentrated under reduced pressure. The residue is extracted with ethyl acetate and the extracts are treated with charcoal and evaporated to an oil. Cooling and agitation of the oil with dry ether affords a crystalline solid (2.8 g.) which is collected. Recrystallization from ethyl acetate yields 4(5)-(4-cyanobutyl)imidazole, m.p. 97°–99° C. The nitrile is obtained analytically pure by chromatographing on a column of silica gel and eluting with ethanol-ethylacetate.

The nitrile is converted into its hydrochloride salt (2.22 g) and dissolved in anhydrous methanol (5 ml). The solution is cooled and stirred during the slow addition of a saturated methanolic solution of hydrogen chloride.

After addition the solution is stirred at 0° C. for three hours and diluted with ether. The imino-ether hydrochloride separates as an oil which is washed twice with cold ether and dissolved in absolute alcohol (5 ml.). An ice cold solution prepared from anhydrous ammonia (2.1 g) and ethanol (15 ml) is added rapidly with external cooling. After one hour at 0° C. the mixture is allowed to attain room temperature. Ammonium chloride is filtered off and the filtrate is evaporated to an oil. A slight excess of ethanolic hydrogen chloride is added and the solution is again evaporated. Trituration of the residue with a little absolute alcohol followed by recrystallization from ethanol-ether affords pure 5-(4(5)-imidazolyl)valeramidine dihydrochloride, m.p. 221°–222° C.

EXAMPLE 49

Preparation of N-methyl-N'-[3-(4(5)-imidazolyl)propyl] thiourea

Methyl isothiocyanate (2.92 g) is added to a solution of 4(5)-(3-aminopropyl)imidazole (5.0 g.) in chloroform (100 ml) and dimethylformamide (10 ml). The resultant solution is heated under reflux for 2.5 hours and evaporated to dryness. The residue is treated with ethanolic hydrogen chloride which affords a hygroscopic hydrochloride. This is recrystallized from ethanol-ether and converted to the base with aqueous potassium carbonate. Evaporation followed by extraction with ethanol yields the crude base which after recrystallisation from water yields pure N-methyl-N'-(3-(4(5)-imidazolyl)propyl)thiourea, m.p. 135°–137° C.

EXAMPLE 50

Preparation of N-[4-(4(5)-imidazolyl)butyl]thiourea

N-Benzoyl-N'-[4-(4(5)-imidazolyl)butyl]thiourea hydrothiocyanate (1.5 g) is added with stirring to 10% aqueous potassium hydroxide (30 ml) at 65°–70° C. After 15 minutes the mixture is cooled, acidified with dilute hydrochloric acid, and after two hours at 5° C. is filtered from the benzoic acid which precipitates. The filtrate is basified with anhydrous potassium carbonate and concentrated to dryness under reduced pressure to yield a residue which is extracted with hot ethanol. The extract is concentrated to 5 ml and cooled to yield colourless crystals. The latter, after being crystallized from water (9 ml) furnishes N-[4-(4(5)imidazolyl)-butyl]thiourea, m.p. 166°–167° C.

EXAMPLE 51

Preparation of N-methyl-N'-[4-(4(5)-imidazolyl)butyl]thiourea

4(5)-(4-Aminobutyl)imidazole (15.0 g. containing approximately 12% w/w ethanol) is dissolved in warm acetonitrile (100 ml). The solution is filtered, methyl isothiocyanate (7.3 g) is added and the resultant solution is heated under reflux for 1.5 hours. Following concentration, the residual oil is triturated several times with warm isopropyl acetate which affords the thiourea in crystalline form.

Recrystallization from acetonitrile-isopropyl acetate yields N-methyl-N'-[4-(4(5)-imidazolyl)butyl]thiourea. After further recrystallization from acetonitrile, followed by recrystallization from water, the product melts at 127°–128° .

EXAMPLE 52

Preparation of N-isopropyl-N'-(4-(4(5)-imidazolyl)butyl) thiourea

4(5)-(4-aminobutyl)imidazole (1.3 g) is caused to react with isopropyl isothiocyanate (1.0 g) by a procedure similar to that described in Example 51. Recrystallization from aqueous isopropyl alcohol affords N-isopropyl-N'-(4-(4(5)-imidazolyl)butyl)thiourea m.p. 138°–139° C.

EXAMPLE 53

Preparation of N-methyl-N'-[5-(4(5)-imidazolyl)pentyl]thiourea.

i. A mixture of 1-bromo-7-phthalimidoheptan-2-one (obtainable from 8-aminocaproic acid) (60.0 g) and formamide (360 ml) is heated at 180°–185° C for two hours. Following removal of excess formamide by distillation under reduced pressure, the residue is hydrolysed by heating under reflux with 6N hydrochloric acid (1.8 l.) for 18 hours. After cooling to 0° C and filtering to remove phthalic acid, the filtrate is concentrated under reduced pressure and the residue extracted with hot ethanol and again concentrated. The residual amine hydrochloride is converted to the free base by passage down an ion-exchange resin (OH—) and elution with methanol. The base obtained is converted into the picrate with picric acid (82.5 g) in water. The picrate is recrystallized several times from water affording 4(5)-(5-amino-pentyl)imidazole dipicrate, m.p. 209°–211° C. Melting point of an analytically pure sample (from nitromethane) is 210°–211° C.

The picrate is treated with hydrochloric acid in the usual way, yielding the amine dihydrochloride which is finally converted to 4(5)-(5-aminopentyl)imidazole, m.p. 45°–48° C., by passage down ion-exchange resin (OH—). ii. A solution of methyl isothiocyanate (2.92 g) and 4(5)-(5-aminopentyl)imidazole (6.13 g) in acetonitrile (40 ml) is heated under reflux for three hours. Cooling, followed by recrystallization of the product from acetonitrile affords N-methyl-N'-[5-(4(5)-imidazolyl)pentyl]thiourea, m.p. 108°–109° C.

EXAMPLE 54

Preparation of N-methyl-N'-(4-(5-bromo-4-imidazolyl)butyl) thiourea i. To a stirred mixture of (4(5)-(4-aminobutyl)imidazole (15.8 g, containing 8% weight/weight ethanol) in concentrated sulphuric acid (250 ml) is added silver sulphate (31.2 g). Light is excluded from the reaction mixture and bromine (10.75 ml) is added, followed by sulphuric acid washings (25 ml). The reaction mixture is stirred in the dark for 2–5 days, filtered and the precipitate washed with sulphuric acid (50 ml). The combined filtrates are added to water (1L.) and neutralised to pH 6–7 with sodium carbonate with cooling. Following filtration, the filtrate is concentrated under reduced pressure. The residue is converted to the hydrochloride using hydrogen chloride in isopropyl alcohol. The hydrochloride is passed down Amberlite ion-exchange resin IRA 401 ($SO_4^{--}$) and eluted with water. The eluate is concentrated under reduced pressure and the residue extracted with methanol and diluted with ethanol yielding 5-bromo-4-aminobutylimidazole sulphate (15.8 g). Recrystallization from water-methanol-ethanol affords the analytically pure product (11.2 g), m.p. 92°–95° C. ii. A solution of 5-bromo-4-aminobutylimidazole (2.39 g) prepared from the hydrochloride and potassium carbonate) and methyl isothiocyanate (0.73 g) in ethanol (10 ml) is heated under reflux for 2 hours. Concentration followed by recrystallization of the residue twice from ethanolether affords N-methyl-N'-(4-(5-bromo-4-imidazolyl)butyl) thiourea m.p. 153°–155° C.

EXAMPLE 55

Preparation of N-methyl-N'-(4-(3-(1,2,4-triazolyl)butyl) thiourea i. 5-Phthalimidovaleroyl chloride (90.0 g) is added portionwise to a suspension of thiosemicarbazide (34.0 g) in anhydrous pyridine (220 ml) at 0°–5° C. After addition the mixture is kept at 0° C for 1 hour and set aside overnight at room temperature. Following addition to water (2 l.) the white solid is collected and washed with 50% aqueous acetic acid and then water. Recrystallization from nitromethane affords 1-(5-(phthalimidovaleroyl) thiosemicarbazide (69 g), m.p. 196° C.

ii. 1-(5-(Phthalimidovaleroyl))thiosemicarbazide (69 g) dissolved in a solution prepared from sodium (6.25 g) in ethanol (860 ml) is heated under reflux for 16 hours. Concentration to low bulk, followed by the addition of ice-water affords a white crystalline solid, which is collected and washed successively with water, ethanol and ether to give 3-(4-phthalimidobutyl)-1,2,4-triazoline-5-thione (33 g), m.p. 223°–225° C.

iii. The triazolinethione (30.5 g) is dissolved in ethanol (360 ml) and heated under reflux with stirring for 2 hours in the presence of Raney Nickel (90 g). Filtration, followed by concentration and the addition of water affords 3-(4-phthalimidobutyl)-1,2,4-triazole (13.3 g) m.p. 169°–171° C. A sample recrystallised from water has m.p. 171°–172° C.

iv. The phthalimido derivative (13.0 g.) is hydrolysed with 5N hydrochloric acid for 8 hours under reflux. Following cooling and removal of phthalic acid, the filtrate is concentrated. The solid residue is triturated with ethanol-ether (1:1) and filtered to afford 3-(4-aminobutyl)-1,2,4-triazole dihydrochloride (10.0 g), m.p. 171°–172° C.

v. The amine hydrochloride (5.0 g) is converted into its free base with aqueous potassium carbonate by concentration followed by extraction with ethanol-ether (3:1). The base is dissolved in ethanol and caused to react with methylisothiocyanate (1.87 g) in ethanol. The product obtained is recrystallized from water followed by ethanol-ether to afford N-methyl-N'-(4-(3-(1,2,4-triazolyl)butyl)thiourea (3.15 g), m.p. 133°–134° C.

EXAMPLE 56

Preparation of N-methyl-N'-(4-(2-pyridyl)butyl)thiourea i. 2-(3-cyanopropyl)pyridine (14.6 g) in dry ether (100 ml) is added dropwise to a stirred suspension of lithium aluminium hydride (9.5 g) in dry ether (300 ml). The mixture is heated under reflux for 3 hours, cooled and treated successively with water, aqueous sodium hydroxide and water. Extraction with chloroform, followed by fractionation affords. 2-(4-aminobutyl)pyridine (6.7 g), b.p. 100°–101° C/1.0 mm.

ii. The reaction of 2-(4-aminobutyl)pyridine (3.0 g) and methyl isothiocyanate (1.6 g) in ethanol (25 ml) for 0.5 hours followed by chromatography of the product on silica and elution with ethyl acetate affords N-methyl-N'-(4-(2-pyridyl)butyl)thiourea (3.0 g) as a colourless oil.

EXAMPLE 57

Preparation of N-methyl-N'-(4-(2-thiazolyl)butyl)thiourea i. Liquid ammonia (20 g) and 4-phthalimidovaleronitrile (67 g) is added to a cooled solution of hydrogen sulphide (50 g) in methyl alcohol (500 ml). The sealed reaction vessel is the heated at 40° for 3 days with stirring. Concentration followed by recrystallization from isopropyl acetate yields 4-phthalimidothiovaleramide, m.p. 143°–146° C.

ii. A mixture of the thioamide (11.0 g) and bromacetal (8.3 g) is heated for 1 hour on the steam-bath. Following filtration and washing with water, the crude product is dissolved in hydrochloric acid and precipatated by the addition of saturated sodium acetate. Recrystallization from isopropyl alcohol-water finally yields 2-(4-phthalimidobutyl)thiazole (5.22 g) m.p. 86°–88° C.

iii. 2-(4-Phthalimidobutyl)thiazole (5.0 g) is hydrolysed with hydrochloric acid in the usual way. The amine hydrochloride obtained is basified with potassium carbonate and extracted with ether-ethanol (3:1) to give 2-(4-amino-butyl)thiazole as a colourless oil.

The reaction of the amine (2.0 g) and methyl isothiocyanate (0.98 g) in ethanol (10 ml) for 1 hour, followed by chromatography of the product on silica gel with ethyl acetate as eluent gives N-methyl-N'-(4-(2-thiazolyl)butyl) thiourea (2.5 g) as a colourless oil. Formation of the hydrobromide salt yields a crystalline solid, m.p. 130°–132° C.

EXAMPLE 58

N-Methyl-N'-[2-((4-imidazolyl)methylthio)ethyl]thiourea i. (a) A solution of 4(5)-hydroxymethylimidazole hydrochloride (67 g) and cysteamine hydrochloride (56.8 g) in aqueous hydrobromic acid (1 litre, 48%) was heated under reflux overnight. After cooling, the solution was evaporated to dryness and the residual solid washed with ethanol/ether to give 4(5)-[(2-aminoethyl)thiomethyl]imidazole dihydrobromide (156 g.), m.p. 178°–179°.

b. Phthalimidoethanethiol (2 g.) was added portionwise with stirring to a solution of sodium ethoxide (prepared from 0.23 g. of sodium) in ethanol (20 ml.) at 0° under a nitrogen atmosphere. After stirring at 0° for a further 2½ hours, the resulting yellow solution was cooled with an ice-salt bath and a solution of 4(5)-chloromethylimidazole hydrochloride (0.76 g.) in ethanol (5 ml.) was added dropwise over 10 minutes. After addition the mixture was stirred at room temperature overnight, then acidified with ethanolic hydrogen chloride and evaporated to dryness. Addition of water precipitated unreacted phthalimidoethanethiol (0.6 g.) which was removed by filtration. The filtrate was concentrated and basified with aqueous sodium bicarbonate solution to furnish a white precipitate which, on recrystallisation from aqueous ethanol, gave 4(5)-[(2-phthalimidoethyl)thiomethyl]imidazole (0.75 g.) m.p. 136°–137°. A stirred mixture of this phthalimido derivative (0.62 g.) in aqueous hydrobromic acid (40 ml. 18%) was heated under reflux overnight. After cooling to 0°, the resulting clear solution was filtered and the filtrate evaporated to dryness. Recrystallisation of the residue from ethanol gave 4(5)-[(2-aminoethyl)thiomethyl]imidazole dihydrobromide (0.52 g.), m.p. 178°–179°.

c. A suspension of cysteamine hydrochloride (118.8 g.) in ethanol (200 ml., dried over molecular sieves) was added portionwise at 0° to a solution of sodium ethoxide (prepared from 48 g. of sodium) in ethanol (1 litre) under a nitrogen atmosphere. After stirring at 0°, for a further 2 hours, a solution of 4(5)-chloromethylimidazole hydrochloride (80 g.) in ethanol (400 ml.) was added dropwise over 45 minutes while the temperature was maintained at −1° ± 2°. After addition, the mixture was stirred at room temperature overnight, filtered and the filtrate acidified with concentrated hydrochloric acid. The solution was then evaporated to dryness, the residue dissolved in ethanol (1 litre) and a solution of excess picric acid in hot ethanol added. The resulting crude picrate was dissolved in water (2.7 litres) and, after decantation from an insoluble oil, the solution was left to cool to give 4(5)-((2-aminoethyl)-thiomethyl) imidazole dipicrate, m.p. 194°–195°. Treatment of this picrate with aqueous hydrobromic acid followed by extraction with toluene gave the dihydrobromide, m.p. 178°–179°, after evaporation to dryness and recrystallisation of the crude residue from ethanol.

ii. A solution of 4(5)-((2-aminoethyl)thiomethyl) imidazole dihydrobromide (10 g.) in water (25 ml.) was basified to pH 11 by the addition of a solution of potassium carbonate (8.7 g.) in water (25 ml.). The resulting solution was evaporated to dryness, extracted with isopropyl alcohol and the final traces of water removed by azeotroping with isopropyl alcohol. The residual amine was extracted from the inorganic material with isopropyl alcohol, the extracts concentrated to about 70 ml. and a solution of methyl isothiocyanate (2.3 g.) in isopropyl alcohol (5 ml.) added. The reaction mixture was then heated under reflux for 1½ hours and, after cooling, evaporated to dryness. The residual oil was dissolved in acetone, the solution filtered to remove traces of inorganic material, and the filtrate concentrated to give N-methyl-N'-(2-(4-imidazolylmethylthio)ethyl)thiourea (4.1. g.), m.p. 96°–98°. A sample, recrystallised from acetone, had m.p. 98°–99°.

EXAMPLE 59

N-Methyl-N'-[2-((5-methyl-4-imidazolyl)methylthio)ethyl]thiourea i. (a) A solution of 4-hydroxymethyl-5-methylimidazole hydrochloride (30.0 g) and cysteamine hydrochloride (23.0 g.) in acetic acid (200 ml.) was heated under reflux for 10 hours. Following cooling to 15°–20°, the solid which crystallised was collected and washed with isopropyl alcohol to give 4-methyl-5-[(2-aminoethyl)thiomethyl]-imidazole dihydrochloride (45.5 g), m.p. 189°–192°.

b. A solution of 4-hydroxymethyl-5-methylimidazole hydrochloride (30.0 g.) and cysteamine hydrochloride (23.0 g) in concentrated aqueous hydrochoric acid (450 ml.) was heated under reflux for 17 hours. Concentration followed by re-evaporation with water afforded a residue which was dissolved in isopropyl alcohol, concentrated to low bulk and cooled to afford 4-methyl-5-[(2-aminoethyl)thiomethyl]imidazole dihydrochloride (40.6 g.), m.p. 185°–191°.

c. A mixture of 4-hydroxymethyl-5-methylimidazole hydrochloride (15.0 g.), cysteamine hydrochloride (11.5 g.) and a solution of hydrogen bromide in acetic acid (48%, 225 ml.) was heated under reflux for 7 hours. Cooling afforded 4-methyl-5-[(2-aminoethyl)thiomethyl]imidazole dihydrobromide (21.6 g.), m.p. 208°–211°.

ii. Potassium carbonate (7.75 g.) was added to a solution of 4-methyl-5-[(2-aminoethyl)thiomethyl]imidazole dihydrochloride (14.6 g.) in water (120 ml.). The solution was stirred at room temperature for 15 minutes and methyl isothiocyanate (5.15 g.) was added. After heating under reflux for 30 minutes, the solution was slowly cooled to 5°.

The product (13.1 g) was collected and re-crystallised from water to give N-methyl-N'-[2-((5-methyl-4-imidazolyl) methylthio)ethyl]thiourea, m.p. 150°–152°.

EXAMPLE 60

Preparation of N-methyl-N'-[2-(5-isopropyl-4-imidazolyl)-methylthio)ethyl]thiourea.

i. A solution of sodium nitrite (43.8 g.) in water (92 ml.) was added dropwise, with stirring, to a solution of ethyl isobutyrylacetate (100.3 g.) in acetic acid (80 ml.) at 0°. After stirring at 0° for 30 minutes then at room temperature for 3 hours, water (100 ml.) was added and the mixture extracted with ether. The extracts were washed with water, saturated sodium bicarbonate solution and water. After drying (CaSO4), the solution was evaporated to give ethyl 2-oximino-4-methyl-3-oxopentanoate (112 g.) as a crude oil.

A solution of this oximinoketone (219 g.) in ethanol (280 ml.) was added to a suspension of pre-reduced palladised charcoal (10 g., 10%) in ethanol (1 lit.) and saturated ethanolic hydrogen chloride (512 ml.) and the mixture hydrogenated at room temperature and pressure until the theoretical amount of hydrogen was taken up. The mixture was filtered, the filtrate concentrated and ethyl acetate added to give ethyl 2-amino-4-methyl-3-oxopentanoate hydrochloride (230.6 g.) m.p. 129°–131° C(dec.). This aminoketone (50.5 g.) was dissolved in redistilled formamide (180 ml.) and the solution heated at 120° for two hours, 130° for one hour, and finally at 140° for two hours. After cooling, the mixture was filtered and the crystalline product washed with water to give ethyl 4-isopropyl-5-carbethoxy-imidazole (22. g.) m.p. 177°–178°.

This ester (108 g.) was placed in a soxhlet and reduced with lithium aluminium hydride (34.5. g.) in tetrahydrofuran to give 4-hydroxymethyl-5-isopropylimidazole (62.3 g.) m.p. 121°–123°.

ii. By a two-stage process essentially similar to that described in Example 58 (i) and (ii) there was produced from 4-hydroxymethyl-5-isopropylimidazole firstly the intermediate 4-isopropyl-5-[(2-aminoethyl)-thiomethyl]-imidazole dipicrate (m.p. 170°–172.5° C) and finally, after recrystallisation from isopropyl acetate/ether the title compound, m.p. 86°–89° C.

EXAMPLE 61

Preparation of N-Methyl-N'-[2-(3-hydroxy-2-pyridyl) methylthio)ethyl]thiourea

By the method of Example 58 (i) and (ii) 2-hydroxymethyl-3-hydroxy-pyridine was converted first to the intermediate 3-hydroxy-2-[(2-aminoethyl)thiomethyl]pyridine dihydrobromide (m.p. 231°–232° C.) and thence to the title compound (m.p. 130°–133° C., after recrystallisation from water).

EXAMPLE 62

Preparation of N-methyl-N'-[2-(3-pyridazinyl)methylthio)-ethyl]thiourea.

By the method of Example 58 (i) and (ii) 3-hydroxymethylpyridazine was converted first to the intermediate 3-[(2-aminoethyl)thiomethyl]-pyridazine dipicrate (m.p. 145°–148° C) and thence to the title compound (m.p. 110°–111° C, after recrystallisation from acetone/ether).

EXAMPLE 63

Preparation of N-methyl-N'-[2-(5-(2-amino-1,3,4-thiadiazolyl)-methylthio)ethyl]thiourea By the method of Example 58 (i) and (ii) 2-amino-5-hydroxymethyl-1,3,4-thiadiazole was converted first to the intermediate 2-amino-5-[(2-aminoethyl)thiomethyl]-1,3,4-thiadiazole dibromide (m.p. 229°–232° C.) and thence to the title compound (m.p. 143°–145° C, after recrystallisation from aqueous ethanol).

EXAMPLE 64

Preparation of
N-methyl-N'-[3-(4-imidazolylmethylthio)-propyl]thiourea

By the method of Example 58 (i) and (ii) 4(5)-hydroxymethylimidazole was converted first to the intermediate 4(5)-[(3-aminopropyl)thiomethyl]-imidazole dihydrobromide and thence to the title compound (m.p. 118°–120° C, after recrystallisation from water).

EXAMPLE 65

N-methyl-N'-[3-(2-oxazolyl)thiopropyl]thiourea i. Hydrochloric acid (90 ml.) was added to potassium thiocyanate in ethanol (1.8 l.) with stirring. Following filtration from inorganic material, glycollaldehyde (35.9 g.) was added and the resulting solution was heated under reflux for 24 hours. Concentration, followed by cooling afforded a white solid, which following recrystallisation from ethanol afforded oxazole-2-thiol (30 g.), m.p. 143–4.

ii. 3-Bromopropylphthalimide (13.4 g.) was added to a stirred solution of sodium ethoxide (from 1.15 g. sodium) and oxazole-2-thiol (5.1 g.) in ethanol (100 ml.). The resultant solution was heated under reflux for 2.5 hours and concentrated under reduced pressure. The residue was triturated with water (100 ml.) to afford 2-(3-phthalimido propylthio)oxazole (14. g) m.p. 101. Recrystallisation from ethanol gave the pure oxazole m.p. 102-3.

ii. Hydrazine hydrate (5.3. g.) was added carefully to a solution of 2-(3-phthalimidopropylthio)oxazole (10 g.) in ethanol (173 ml.) with stirring. The solution was then heated under reflux for 25 minutes. After cooling, and filtration from phthalhydrazide, the filtrate was concentrated under reduced pressure and the residue was re-evaporated with ethanol to yield crude 2-(3-aminopropylthio)oxazole which was washed twice with ether and dissolved in ethanol (60 ml.). Methyl isothiocyanate (2.54 g.) was added and the solution was heated under reflux for 30 minutes. Following cooling and filtration from insoluble material, the filtrate was concentrated to an oil which was chromatographed on a column of silica gel with ethyl acetate as eluent. The product obtained crystallised from ethanol-ether-n-hexane to give N-methyl-N'-[3-(2-oxazolyl)thiopropyl]thiourea (2.4 g), m.p. 43°–45°.

EXAMPLE 66

N-Methyl-N'-[2-(4-imidazolyl methoxy)ethyl]thiourea i. A stirred suspension of 4-(2-chloroethoxy methyl) imidazole hydrochloride (14.7 g.) and sodium azide (9.8 g.) in dry dimethylformamide (103 ml.) was maintained at 95° for 5 hours and then set aside overnight at room temperature. Following dilution with water and filtration, the filtrate was concentrated and the residue purified by chromatography on a dry column of alumina using ethanol. The product was basified with potassium carbonate (6.5 g.) in water (3. ml.) and the anhydrous residue was extracted with isopropyl alcohol (3 × 50 ml.) Concentration of the extracts afforded 4-(2-azidoethoxymethyl)imidazole (7.2 g.) Hydrogenation of the azido compound (7.2 g.) in isopropyl alcohol (142 ml.) over platinum oxide catalyst (3.0 g.) gave 4-(2-aminoethoxy methyl)imidazole (6.48 g.) A sample of the monopicrate monohydrochloride had m.p. 139°–140° (from nitromethane).

(Found: C, 35.4; H, 3.8; N, 20.5; Cl, 8.8. $C_{12}H_{15}ClN_6O_8$ requires: C, 35.4; H, 3.7; N, 20.7; Cl, 8.7).

ii. 4-(2-Aminoethoxymethyl)imidazole (2.24 g.) was caused to react with methylisothiocyanate (1.21 g.) in isopropyl alcohol (25 ml.) in the usual way. The crude product was purified by chromatography on a column of silica gel with ethyl acetate as eluant and subsequently on a dry column of alumina, using chloroform. The final product was recrystallised from ethyl acetate to give N-methyl-N'-[2-(4-imidazolylmethoxy)ethyl]-thiourea (0.80 g.), m.p. 96°–98°.

EXAMPLE 67

N-Methyl-N'-[3-(2-pyridylamino)propyl]thiourea

A solution of 2-(3-aminopropylamino)pyridine (2.74 g.) and methyl isothiocyanate (1.46 g.) in isopropyl alcohol (50 ml.) was stirred at room temperature for 16 hours Concentration, followed by trituration of the residue under methyl ethyl ketone gave the crude product which, was recrystallized from aqueous ethanol to give N-methyl-N'-[3-(2-pyridylamino)propyl]thiourea (2.45 g.) m.p. 134°-135.5°.

EXAMPLE 68

N-methyl-N'-[2-((4-methyl-5-imidazolyl)methylthio)ethyl]urea

A mixture of 4-methyl-5-((2-aminoethyl)thiomethyl)imidazole (5.1 g.) and methyl isocyanate (2.0 g.) in acetonitrile was heated for 18 hours in a pressure vessel at 100°. After cooling, the solid obtained was collected and recrystallised from isopropyl alcohol-acetonitrile to give N-methyl-N'-[2-((4-methyl-5-imidazolyl) methylthio)ethyl]urea (4.0 g.) m.p. 158°–159°.

EXAMPLE 69

2-[(4-Imidazolyl)methylthio]ethylguanidine sulphate

A solution of 4-((2-aminoethyl)thiomethyl)imidazole (5.8 g.) and S-methyl isothiouronium sulphate (4.8 g.) in water (50 ml.) was heated under reflux for 3 hours. Following concentration to low bulk and acidification with dilute sulphuric acid, ethanol was added. The product obtained was recrystallised from aqueous methanol to give 2-[(4-imidazolyl)methylthio]ethylguanidine sulphate (5.2 g.), m.p. 211°–213°.

EXAMPLE 70

N-(2-[(-4-methyl-5-imidazolyl)methylthio]ethyl)-N'-nitroguanidine

A solution of 4-methyl-5-(2-aminoethyl thiomethyl)imidazole (1.7 g.) and S-methyl-N-nitroisothiourea (1.45 g.) in methanol (35 ml.) was heated at 50°–60° for 2.5 hours and then set aside at room temperature for 48 hours. The crystalline product was filtered off and recrystallised from methanol to give N-(2-[(4-methyl-5-imidazolyl) methylthio]ethyl)-N'-nitroguanidine, m.p. 184°–186°.

EXAMPLE 71

N-methyl-N'-[2-(4-trifluoromethyl-5-imidazolyl)methylthio) ethyl]thiourea

A mixture of ethyl 2-chloro-4,4,4-trifluoroacetate (65.7 g.), distilled formamide (135 g.) and water (11 ml.) was heated at 128°–130° for 1.5 hours. After cooling, an equal volume of ice-cold water was added to give 4-trifluoromethyl-5-carbethoxyimidazole, m.p. 184°–186° (from aqueous methanol).

Reduction of the ester (9.4 g.) with lithium aluminium bydride (2.4 g.) in tetrahydrofuran gave 5-hydroxymethyl-4-trifluoromethylimidazole, isolated at its picrate, m.p. 135.5°–137.5° (from aqueous isopropyl alcohol).

The picrate (5.3 g.) was dissolved in 48% aqueous hydrobromic acid and extracted with toluene to remove picric acid. Cysteamine hydrochloride (1.52 g.) was added to the aqueous phase and the acidic solution heated under reflux for 12 hours. Concentration and trituration of the residue with ethanol-ether gave 4-trifluoromethyl-5-[(2-aminoethyl)thiomethyl]imidazole dihydrobromide (3.2 g.), m.p. 179°–182°. Basification followed by treatment with methyl isothiocyanate gave N-methyl-N'-[2-(4-trifluoromethyl-5-imidazolyl)methylthio)ethyl]thiourea.

EXAMPLE 72

N-methyl-N'-[2-(2-pyrimidyl)methylthio)ethyl]thiourea

A mixture of 5-bromo-2-hydroxymethylpyrimidine (5.6 g.) and magnesium oxide (5.6 g.) in water/ethanol (2:1) was submitted to hydrogenolysis over 10% palladised charcoal for 0.5 hours. Filtration, concentration and ether extraction from an aqueous solution of the residue afforded 2-hydroxymethylpyrimidine (1.85 g.) as a mobile liquid.

The reaction of 2-hydroxymethylpyrimidine with cysteamine followed by further reaction of the product with methyl isothiocyanate, according to the methods described in Example 58 gave N-methyl-N'-[2-(2-pyrimidyl)methylthio)-ethyl]thiourea.

EXAMPLE 73

N-methyl-N'-[2-(2-pyrazinyl)methylthio)ethyl]thiourea i. 2-chloromethylpyrazine (6.4 g.) was added over 20 minutes to a solution freshly prepared from sodium (0.23 g.) in ethanol (50 ml) to which cysteamine hydrochloride (5.7 g.) had been added gradually at 0° and stirred at this temperature for 2 hours. The suspension finally obtained was stirred at room temperature overnight, acidified with hydrochloric acid (pH 5) and concentrated under reduced pressure. The dry residue was extracted with ethanol and the extracts filtered and concentrated to give the crude product. Extraction with isopropyl alcohol, with the removal of some polymeric material and the addition of ether gave a cream coloured solid (3.5 g.) which was recrystallised from ethanol-ether to furnish 2-[(2-aminoethyl)thiomethyl]-pyrazine hydrochloride m.p. 144°–146°.

ii. The amine hydrochloride (1.6 g.) was converted into the free base using potassium carbonate and reacted with methyl isothiocyanate (0.61 g.) in ethanol in the usual way. Recrystallisation from ethanol furnished N-methyl-N'-[2-(2-pyrazinyl)methylthio)ethyl]thiourea (0.88 g.) m.p. 99.5°–100°.

EXAMPLE 74

Preparation of N-methyl-N'-[2-((4-bromo-3-isothiazolyl)methylthio)ethyl]thiourea The reaction of 4-bromo-3-(bromomethyl)isothiazole (8.5 g.) with cysteamine (from cysteamine hydrochloride (3.76 g) was performed under conditions similar to those described in Example 57. From the reaction there was obtained 4-bromo-3-[(2-aminoethyl)thiomethyl]isothiazole hydrobromide, which, following recrystallisation from ethanol-ether and acetonitrile, gave needles (4.05 g.) m.p. 111°–112°. The amine base (2.73 g.) was isolated by basification with sodium bydroxide and extraction with chloroform and then dissolved in ethanol and treated with methyl isothiocyanate (0.78 g.) The solution was heated under reflux for 30 minutes, concentrated and the residue triturated with ether to yield the crystalline thiourea (2.9 g.)m.p. 60°–61°. Recrystallisation from isopropyl acetate gave N-methyl-N'-[2-((4-bromo-3-isothiazolyl)methylthio)ethyl]thiourea (2.3 g.) as needles, m.p. 62°–63°.

EXAMPLE 75

N-cyano-N'-methyl-N''-[2-((4-methyl-5-imidazolyl)-methylthio)-ethyl]guanidine

A solution of 4-methyl-5-[(2-aminoethyl)thiomethyl]-imidazole (17.0 g.) and N-cyano-N',S-dimethylisothiourea (11.2 g.) in acetonitrile (500 ml) was heated under reflux for 24 hours. Following concentration, the residue was chromatographed on a column of silica gel with acetonitrile as eluant and the product obtained was finally recrystallised from acetonitrile-ether to yield N-cyano-N'-methyl-N''-[2-((methyl-5-imidazolyl)methylthio)ethyl]guanidine m.p. 141°–2°.

When N-cyano-N'-methyl-N''-[2-((4-methyl-5-imidazolyl)-methylthio)ethyl]guanidine is treated with concentrated hydrochloric acid at 100° for 4 hours, the product which is recrystallised from ethanol-ether is N-methyl-N'-[2-((4-methyl-5-imidazolyl)methylthio)ethyl]guanidine dihydrochloride, m.p. 204°–206°.

(Found: C, 35.8; H, 6.5; N, 22.7; S, 10.8; Cl, 23.7. $C_9H_{17}N_5S.2HCl$ requires: C, 36.8; H, 6.4; N, 23.3; S, 10.7; Cl, 23.6).

EXAMPLE 76

N-Cyano-N'-ethyl-N''-[2-((4-methyl-5-imidazolyl)methylthio)ethyl]guanidine a. Anhydrous ethylamine (9.0 g) was added to a solution of N-cyano-N'-[2-((4-methyl-5-imidazolyl)-methylthio)ethyl]-S-methylisothiourea (5.0 g), prepared from 4-methyl-5-[(2-aminoethyl)thiomethyl]imidazole by the procedure of Example 97, in ethanol. The solution was heated under reflux for 8 hours and concentrated under reduced pressure. The residue was dissolved in isopropyl alcohol, filtered, and diluted with water. The white solid obtained was recrystallised from isopropyl alcohol-ether to yield N-cyano-N'-ethyl-N''-[2-((4-methyl-5-imidazolyl)methylthio)ethyl]guanidine, m.p. 118°–120°.

(Found: C, 49.6; H, 6.8; N, 31.2; S, 11.7. $C_{11}H_{18}N_6S$ requires: C, 49.6; H, 6.8; N, 31.6; S, 12.0).

b. (i) A solution of 4-methyl-5-[(2-aminoethyl)thiomethyl]-imidazole (6.9 g) and ethyl isothiocyanate (3.84 g) in ethanol was heated under reflux for 2 hours.

Concentration followed by recrystallisation of the residue from aqueous ethanol gave N-ethyl-N'-[2-((4-methyl-5-imidazolyl)methylthio)ethyl]thiourea (9.0 g), m.p. 140°–141°.

(Found: C, 46.5; H, 7.1; N, 21.7; S, 25.1. $C_{10}H_{18}N_4S_2$ requires: C, 46.5; H, 7.0; N, 21.7; S, 24.8).

ii. Reaction of the thiourea with excess lead cyanamide by a procedure similar to that described in Example 91, refluxing for 24 hours, afforded N-cyano-N'-ethyl-N''-[2-((4-methyl-5-imidazolyl)methylthio)ethyl]guanidine.

EXAMPLE 77

N-Cyano-N'-[2-((4-methyl-5-imidazolyl)methylthio)ethyl]-guanidine

A solution of N-cyano-N'-[2-((4-methyl-5-imidazolyl)-methylthio)ethyl]-S-methylisothiourea (2.69 g) in saturated ammoniacal ethanol (100 ml) was heated in a pressure vessel for 16 hours at 95°. Following concentration, the residue was chromatographed on a column of silica gel with ethyl acetate as eluant and finally recrystallized from acetonitrile to give N-cyano-N'-[2-((4-methyl-5-imidazolyl) methylthio)ethyl]guanidine (0.9 g), m.p. 125°–127°.

(Found: C, 45.2; H, 5.9; N, 35.1; S, 13.3; $C_9H_{14}N_6S$ requires: C, 45.4; H, 5.9; N, 35.3; S, 13.5).

EXAMPLE 78

N-[2-((4-Bromo-5-imidazolyl)methylthio)ethyl]-N'-cyano-N''-methylguanidine

The sequential reaction of dimethyl-N-cyanoimidodithiocarbonate (0.99 g) with 4-bromo-5-[(2-aminoethyl)thiomethyl] imidazole (1.6 g), prepared by the procedure of Example 58, and excess methylamine by the procedure described in Example 98 afforded N-[2-((4-bromo-5-imidazolyl)methylthio)ethyl]-N'-cyano-N''-methylguanidine (1.45 g), m.p. 144°–146° (from nitromethane).

(Found: C, 34.3; H, 4.2; N, 26.7; S, 10.1; $C_9H_{13}BrN_6S$ requires: C, 34.1; H, 4.1; N, 26.5; S, 10.2).

EXAMPLE 79

N-[2-((2-Amino-4-imidazolyl)methylthio)ethyl]-N'-cyano-N''-methyl guanidine

Freshly prepared sodium amalgam (90 g) is added over 75 minutes to a stirred solution of serine ethyl ester dihydrochloride (3.0g) in water/ethanol (2:1), the temperature being maintained within the range of from −12° to 10° and the pH at about 2.5 by the addition of 5N hydrochloric acid. After a further 45 minutes the mixture is allowed to warm to 10° and the precipitated free mercury is removed. Cyanamide is added and the mixture warmed to 50° for 30 minutes, left at 0° for 18 hours and evaporated to dryness. After washing with ether to remove any unchanged cyanamide, the residue is extracted with hot ethanol and heated with hot ethanolic picric acid. Concentration and cooling of the solution gives 2-amino-4-hydroxymethylimidazole picrate.

Reaction of 2-amino-4-hydroxymethylimidazole hydrochloride (which is obtained by treating the picrate salt with hydrochloric acid) with cysteamine hydrochloride by the procedure of Example 58 gives 2-amino-4-[(2-aminoethyl)-thiomethyl]imidazole.

By the procedure of Example 75, 2-amino-4-[(2-aminoethyl)-thiomethyl]imidazole is reacted with N-cyano-N',S-dimethylisothiourea to give the title compound.

EXAMPLE 80

| Ingredients | Amounts |
| --- | --- |
| N-Cyano-N'-methyl-N''-[2-((4-methyl-5-imidazolyl)methylthio)ethyl]guanidine | 150 mg. |
| Mepyramine | 75 mg. |
| Sucrose | 75 mg. |
| Starch | 25 mg. |
| Talc | 5 mg. |
| Stearic Acid | 2 mg. |

The ingredients are screened, mixed and filled into a hard gelatin capsule.

EXAMPLE 81

| Ingredients | Amounts |
| --- | --- |
| N-[2-((4-Methyl-5-imidazolyl)methylthio)-ethyl]-N'-nitroguanidine | 200 mg. |
| Mepyramine | 100 mg. |
| Lactose | 100 mg. |

The ingredients are screened, mixed and filled into a hard gelatin capsule.

EXAMPLE 82

By the procedure of Example 58, using as the starting materials 2-hydroxymethylthiazole and 4-hydroxymethylthiazole, were produced the following intermediate amine salts:

2-[(2-aminoethyl)thiomethyl]thiazole dihydrobromide, m.p. 144°–147.5° C.

4-[(2-aminoethyl)thiomethyl]thiazole dihydrobromide, m.p. 197°–203° C.

These amine salts were converted to the free bases and reacted with S-methylisothiouronium sulphate by the procedure of Example 69 to give the following products:

2-(2-thiazolylmethylthio)ethylguanidine sulphate
2-(4-thiazolylmethylthio)ethylguanidine sulphate.

EXAMPLE 83

Reaction of 2-[(2-aminoethyl)thiomethyl]thiazole with S-methyl-N-nitroisothiourea by the procedure of Example 70 gives N-nitro-N'-[2-(2-thiazolylmethylthio)ethyl]guanidine.

Also, reaction of the same starting material with N,S-dimethyl-N'-nitroisothiourea gives N-methyl-N'-nitro-N''-[2-(2-thiazolylmethylthio)ethyl]guanidine.

EXAMPLE 84

N-Cyano-N'-methyl-N''-[2-(2-thiazolylmethylthio)ethyl]-guanidine

Reaction of [(2-aminoethyl)thiomethyl]thiazole (from the dihydrobromide 20.2 g) with N-cyano-N',S-dimethylisothiourea (7.75 g) by a procedure similar to that described in Example 75, afforded N-cyano-N'-methyl-N''-[(2-(2-thiazolylmethylthio)ethyl]guanidine, m.p. 120°–122.5°, following chromatography on silica gel with alcohol.

(Found: C, 42.3; H, 5.1; N, 27.2; S, 25.3. $C_9H_{13}N_5S_2$ requires: C, 42.3; H, 5.1; N, 27.4; S, 25.1). Hydrolysis of N-cyano-N'-methyl-N''-[2-(2-thiazolylmethylthio)ethyl]guanidine by treating with concentrated hydrochloric acid at 100° for 4 hours gives N-methyl-N'-[2-(2-thiazolylmethylthio)ethyl]guanidine dihydrochloride.

EXAMPLE 85

Reaction of N-cyano-N'-[2-(2-thiazolylmethylthio)ethyl]-S-methylisothiourea, prepared by reacting 2-[(2-aminoethyl) thiomethyl]thiazole with dimethyl-N-cyanoimidothio carbonate in ethanol by the procedure of Example 97, with ethylamine in ethanol under reflux for 8 hours gives N-cyano-N'-ethyl-N''-[2-(2-thiazolylmethylthio)ethyl]-guanidine.

Similarly, using propylamine the product is N-cyano-N'-propyl-N''-[2-(2-thiazolylmethylthio)ethyl]-guanidine.

EXAMPLE 86

N-Cyano-N'-methyl-N''-[2-(5-thiazolylmethylthio)ethyl]-guanidine i. The reaction of 5-hydroxymethylthiazole (2.01 g) with cysteamine hydrochloride (1.99 g) in aqueous hydrobromic acid by the method described in Example 58 gave 5-((2-aminoethyl)thiomethyl)thiazole dihydrobromide (4.85 g) m.p. 191°-4° (from methanol).

ii. The reaction of 5-((2-aminoethyl)thiomethyl)thiazole (2.24 g) with methyl isothiocyanate (0.94 g) in ethanol (10 ml) gave a thiourea which was purified by chromatography on a column of silica gel with ethyl acetate as eluant. Recrystallisation from isopropyl acetate-methyl ethyl ketone-ether gave N-methyl-N'-[2-(5-thiazolylmethylthio)ethyl]thiourea (2.1 g) m.p. 86°-88°.

iii. The reaction of N-methyl-N'-[2-(5-thiazolylmethylthio)ethyl]thiourea with lead cyanamide by the procedure of Example 91, refluxing for 24 hours gives the title compound.

EXAMPLE 87

N-Cyano-N'-methyl-N''-[2-((2-amino-4-thiazolyl)methylthio)-ethyl]guanidine i. A mixture of 2-amino-4-chloromethylthiazole hydrochloride (9.0 g) and cysteamine hydrochloride (5.53 g) in acetic acid (100 ml) was heated under reflux for 18 hours. The crude product obtained after concentration was treated with picric acid in ethanol to afford 2-amino-4-[(2-aminoethyl)thiomethyl]thiazole dipicrate, m.p. approximately 200°-210° (from ethanol).

ii. The picrate was converted into the free base by addition of hydrochloric acid, removal of picric acid by toluene extraction, basification with potassium carbonate and extraction of the aqueous residue with ethanol-ether. Reaction of the base (1.89 g) with methyl isothiocyanate (0.73 g) in ethanol (10 ml) gave the crude thiourea. Chromatography on a column of silica gel with ethyl acetate as eluant, followed by recrystallisation from isopropyl alcohol-isopropyl acetate gave N-methyl-N'-[2-((2-amino-4-thiazolyl)methylthio)ethyl]thiourea (1.0 g)., m.p. 136°-140°.

iii. Reaction of N-methyl-N'-[2-((2-amino-4-thiazolyl)-methylthio)ethyl]thiourea with lead cyanamide by the procedure of Example 91, refluxing for 24 hours, gives the title compound.

EXAMPLE 88

The following hydroxymethyl and halomethyl thiazoles are converted to the corresponding (2-aminoethyl)thiomethylthiazoles by the procedure of Example 58:

2-hydroxymethyl-4-methylthiazole
4-chloromethyl-2-methylthiazole
2-chloro-4-chloromethylthiazole and using the (2-aminoethyl)thiomethylthiazoles as starting materials in the procedure of Example 75 gives the following products, respectively:

N-cyano-N'-methyl-N''-[2-((4-methyl-2-thiazolyl)-methylthio)ethyl]guanidine

N-cyano-N'-methyl-N''-[2-((2-methyl-4-thiazolyl)-methylthio)ethyl]guanidine.

N-[2-((2-chloro-4-thiazolyl)methylthio)ethyl]-N-cyano-N''-methylguanidine.

EXAMPLE 89

2-Hydroxy-4-thiazolecarboxylic acid is converted to the methyl ester and the ester is reduced with lithium aluminium hydride in tetrahydrofuran to give 2-hydroxy-4-hydroxymethylthiazole. By the procedure of Example 58 this compound is converted to 4-[(2-aminoethyl)thiomethyl]-2-hydroxythiazole. Using this compound as the starting material in the procedure of Example 84 gives N-[2-((2-hydroxy-4-thiazolyl)methylthio)ethyl]-N-cyano-N''-methylguanidine.

EXAMPLE 90

| Ingredients | Amounts |
| --- | --- |
| N-cyano-N'-methyl-N''-[2-(2-thiazolyl-methylthio)ethyl]guanidine | 150 mg. |
| Mepyramine | 75 mg. |
| Sucrose | 75 mg. |
| Starch | 25 mg. |
| Talc | 5 mg. |
| Stearic acid | 2 mg. |

The ingredients are mixed and filled into a hard gelatin capsule.

EXAMPLE 91

N-Cyano-N'-[2-(3-isothiazolylmethylthio)ethyl]-N''-methylguanidine a. (i) A solution was prepared by the gradual addition of cysteamine hydrochloride (2.03 g) to sodium (0.83 g) dissolved in ethanol (50 ml) with stirring at 0° under a nitrogen atmosphere. After stirring for 2 hours at 0°, 3-bromomethylisothiazole (3.2 g) was added dropwise over 15 minutes at 0°, the reaction mixture subsequently being set aside overnight at room temperature. Following acidification to pH 3.5 with hydrochloric acid, concentration and re-evaporation with ethanol, the residue was dissolved in ethanol, filtered and concentrated to yield 3-[(2-aminoethyl)thiomethyl]isothiazole hydrochloride (3.5 g). This was converted directly to the free base by treatment with aqueous potassium carbonate and extraction with ether. The extracts were dried over magnesium sulphate, filtered and concentrated to yield the amine base as an oil (1.56 g). The amine was dissolved in ethanol (10 ml), methyl isothiocyanate (0.66 g) added, and the solution heated under reflux for 30 minutes. Concentration, followed by purification of the crude product by chromatography on a column of silica gel with ethyl acetate as eluant followed by chromatography on a column of alumina with benzene/ethyl acetate gave N-methyl-N'-[2-(3-isothiazolylmethylthio)ethyl]-thiourea.

(Found: C, 38.9; H, 5.4; N, 16.5; S, 38.3. $C_8H_{13}N_3S_3$ requires: C, 38.8; H, 5.3; N, 17.0; S, 38.9.)

ii. Lead cyanamide (52.6 g) was added to a solution of N-methyl-N'-[2-(3-isothiazolylmethylthio)ethyl]thiourea (17.7 g) in acetonitrile (500 ml) containing dimethylformamide (50 ml). The mixture was stirred under reflux for 48 hours, then filtered and concentrated. The product was chromatographed on silica gel with ethyl acetate as eluant and recrystallised from isopropyl acetate-ether to give N-cyano-N'-[2-(3-isothiazolylmethylthio)ethyl]-N''-methylguanidine, in a crystalline form, m.p.. 63°–64°. Further recrystallisation from isopropyl acetate afforded the cyanoguanidine in a crystalline form, m.p. 91°–92°.

(Found: C, 42.6; H, 5.2; N, 27.4; S, 25.4; $C_9H_{13}N_5S_2$ requires: C, 42.3; H, 5.1; N, 27.4; S, 25.1).

b. (i) The reaction of dimethyl-N-cyanoimidodithiocarbonate (1.50 g) with 3-[(2-aminoethyl)thiomethyl]isothiazole (1.70 g) afforded N-cyano-N'-[2-(3-isothiazolylmethylthio)-ethyl]-S-methylisothiourea. Recrystallisation from isopropyl acetate afforded 0.68 g, m.p. 85°–87°.

(Found: C, 39.7; H, 4.4; N, 20.6; S, 35.4; $C_9H_{12}N_4S_3$ requires: C, 39.7; H, 4.4; N, 20.6; S, 35.3).

ii. The reaction of N-cyano-N'-[2-(3-isothiazolylmethylthio)ethyl]-S-methylisothiourea (0.27 g) with excess methylamine and recrystallisation of the product from isopropyl acetate afforded N-cyano-N'-[2-(3-isothiazolylmethylthio)ethyl]-N''-methylguanidine (0.12 g), m.p. 91°–93°.

(Found: C, 42.4; H, 5.1; N, 27.3; S, 25.2; $C_9H_{13}N_5S_2$ requires: C, 42.3; H, 5.1; N, 27.3; S, 25.2;

EXAMPLE 92

The reaction of 4-bromo-3-(bromomethyl)isothiazole (8.5 g) with cysteamine (from cysteamine hydrochloride, 3.76 g) was performed under conditions similar to those described in Example 91. From the reaction there was obtained 4-bromo-3-[(2-aminoethyl)thiomethyl]isothiazole hydrobromide, which, following recrystallisation from ethanol-ether and acetonitrile, gave needles (4.05 g) m.p. 111°–112°. The amine base (2.73 g) was isolated by basification with sodium hydroxide and extraction with chloroform and then dissolved in ethanol and treated with methyl isothiocyanate (0.78 g). The solution was heated under reflux for 30 minutes, concentrated and the residue triturated with ether to yield the crystalline thiourea (2.9 g) m.p. 60°–61°. Recrystallisation from isopropyl acetate gave N-methyl-N'-[2-((4-bromo-3-isothiazolyl)methylthio)ethyl]thiourea (2.3 g) as needles, m.p. 62°–63°: Reaction of N-methyl-N'-[2-((4-bromo-3-isothiazolyl)methylthio)ethyl]thiourea with lead cyanamide by the procedure of Example 91 gives N-cyano-N'-[2-((4-bromo-3-isothiazolyl)methylthio)ethyl]-N''-methylguanidine. Hydrolysis of the above product according to the procedure of Example 84 gives N-[2-((4-bromo-3-isothiazolyl)methylthio) ethyl]-N'-methylguanidine hydrochloride.

EXAMPLE 93

Reacting 4-hydroxymethyl-3-methylisothiazole (3.0 g) with cysteamine hydrochloride (2.8 g) in 48% aqueous hydrobromic acid (50 ml) by the procedure of Example 58 gives 3-methyl-4-[(2-aminoethyl)thiomethyl]-isothiazole hydrobromide. Treatment of this intermediate with aqueous potassium carbonate, extracting with chloroform, drying the chloroform extract over magnesium sulphate and concentrating gives the free base, 5.0 g. of which is then reacted with methyl isothiocyanate (1.94 g) in ethanol (25 ml) under reflux for 30 minutes. The product is purified on a column of alumina and elution with benzene gives N-methyl-N'-[2-((3-methyl-4-isothiazolyl)methylthio)ethyl]thiourea. Reaction of this product by the procedure of Example 91 gives N-cyano-N'-methyl-N''-[2-((3-methyl-4-isothiazolyl)-methylthio)ethyl]guanidine.

Using 3-bromomethyl-5-chloroisothiazole as the starting material in the above procedure, the product is N-[2-((5-chloro-3-isothiazolyl)methylthio)ethyl]-N'-cyano-N''-methylguanidine.

EXAMPLE 94

2-(3-Isothiazolylmethylthio)ethylguanidine sulphate

Reacting 3-[(2-aminoethyl)thiomethyl]isothiazole with S-methylisothiouronium sulphate by the procedure of Example 69 gives the title compound.

EXAMPLE 95

Reacting 3-[(2-aminoethyl)thiomethyl]isothiazole with S-methyl-N-nitroisothiourea by the procedure of Example 70 gives N-[2-(3-isothiazolymethylthio)ethyl]-N'-nitro-guanidine and reaction of the same starting material with N,S-dimethyl-N'-nitroisothiourea gives N-[2-(3-isothiazolylmethylthio)ethyl]-N'-methyl-N''-nitroguanidine.

EXAMPLE 96

| Ingredients | Amounts |
| --- | --- |
| N-cyano-N'-[2-(3-isothiazolylmethylthio)-ethyl]-N''-methylguanidine | 200 mg. |
| Mepyramine | 100 mg. |
| Lactose | 100 mg. |

The ingredients are mixed and filled into a hard gelatine capsule.

EXAMPLE 97

N-Cyano-N'-[2-((3-hydroxy-2-pyridyl)methylthio)ethyl]-N''-methyl guanidine i. A solution of 2-((2-aminoethyl)thiomethyl)-3-hydroxypyridine (7.5 g) in ethanol was added slowly to a solution of dimethylcyanodithioimidocarbonate (6.0 g) in ethanol, with stirring at room temperature. The mixture was set aside overnight at room temperature. Filtration afforded N-cyano-N'-[2-((3-hydroxy-2-pyridyl)methylthio)-ethyl]-S-methylisothiourea (4.85 g), m.p. 192°–194°. Recrystallisation from aqueous ethanol gave fine needles, m.p. 196°–198°.

(Found: C, 46.6.; H, 5.0; N, 19.8; S, 22.7; $C_{10}H_{14}N_4OS_2$ requires: C, 46.8; H, 5.0; N, 19.8; s, 22.7.)

ii. A mixture of N-cyano-N'-[2-((3-hydroxy-2-pyridyl)-methylthio)ethyl]-S-methylisothiourea (4.8 g) and excess methylamine in ethanol was allowed to stand at room temperature for 2.5 hours. Following concentration under reduced pressure, the residue was chromatographed on a column of silica gel with ethyl acetate containing 15% isopropyl alcohol as eluant and recrystallisation from isopropyl alcohol-petroleum ether gave N-cyano-N'-[2-((3-hydroxy-2-pyridyl)methylthio)ethyl]-N''-methylguanidine (2.4 g), m.p. 146°–148°.

EXAMPLE 98

N-Cyano-N'-[2-((3-bromo-2-pyridyl)methylthio)ethyl]-N''-methyl guanidine i. A solution sodium nitrite (2.28 g) in water (10 ml) was added dropwise to a stirred mixture of 3-amino-2-hydroxymethylpyridine (4.8 g) in aqueous hydrobromic acid (48%, 10 ml) and water (5 ml) at 0.5° C. This solution of the diazonium salt was added to a hot solution of cuprous bromide (2.5 g) in 60% hydromic acid and following cessation of nitrogen evolution the mixture was heated on the steam bath for 0.5 hours, diluted with water and saturated with hydrogen sulphide. Filtration, concentration to low bulk and extraction with chloroform yielded 3-bromo-2-hydroxymethylpyridine (4.8 g). This was dissolved in aqueous hydrobromic acid (48%, 50 ml), cysteamine hydrochloride (3.22 g) added and the solution obtained was heated under reflux for 6 hours. Concentration, followed by recrystalliation from aqueous ethanol afforded 2-((2-aminoethyl)thiomethyl)-3-bromopyridine dihydrobromide (6.1 g), m.p. 252°–254°.

(Found: C, 23.7; H, 3.4; N, 6.7; S, 7.9; $C_8H_{11}BrN_2S.2HBr$ requires: C, 23.5; H, 3.2; N, 6.9; S, 7.8).

ii. Sequential reaction of dimethylcyanodithioimidocarbonate with 2-((2-aminoethyl)thiomethyl)-3-bromopyridine) and excess methylamine at room temperature in ethanol, the methylamine being added after initial standing overnight and the solution then allowed to stand for a further four hours, followed by chromatographic purification on a column of silica gel with elution by ethyl acetate and final recrystallisation from ethyl acetate-petroleum ether gave N-cyano-N'-[2-((3-bromo-2-pyridyl)methylthio)ethyl]-N''-methylguanidine m.p. 114°–116°.

(Found: C, 40.6; H, 4.4; N, 21.4; S, 9.8. $C_{11}H_{14}BrN_5S$. requires: C, 40.3; H, 4.3; N, 21.3; S, 9.8).

EXAMPLE 99

N-Cyano-N'-[2-((3-bromo-2-pyridyl)methylthio)ethyl]-N''-ethylguanidine

Sequential reaction of dimethylcyanodithioimidocarbonate with 2-((2-aminoethyl)thiomethyl)-3-bromopyridine and excess ethylamine, followed by chromatographic purification on a column of silica gel with elution by ethyl acetate and final recrystallisation from ethyl acetate-petroleum ether affored N-cyano-N'-[2-((3-bromo-2-pyridyl)methylthio)-ethyl]-N''-ethylguanidine, m.p. 123°–124°.

(Found: C, 42.2; H, 4.7; N, 20.5; S, 9.4; $C_{12}H_{16}BrN_5S$. requires: C, 42.1; H, 4.7; N, 20.5; S, 9.4).

EXAMPLE 100

Sequential reaction of the following amines;
a. 2-[(2-aminoethyl)thiomethyl]-3-aminopyridine.
b. 2-[(2-aminoethyl)thiomethyl]-3-methylpyridine.
c. 4-[(2-aminoethyl)thiomethyl]pyridine.
d. 2-[(2-aminoethyl)thiomethyl]-5-hydroxypyridine.
with dimethylcyanodithioimidocarbonate and then excess methylamine according to the method described in Example 98 (ii) yield respectively the following products:

a. N-cyano-N'-methyl-N''-[2-((3-amino-2-pyridyl)methylthio)-ethyl]guanidine
b. N-cyano-N'-methyl-N''-[2-((3-methyl-2-pyridyl)methylthio)-ethyl]guanidine.
c. N-cyano-N'-methyl-N''-[2-((4-pyridyl)methylthio)ethyl]-guanidine.
d. N-cyano-N'-methyl-N''-[2-((5-hydroxy-2-pyridyl)methylthio)-ethyl]guanidine.

EXAMPLE 101

| Ingredients | Amounts |
|---|---|
| N-cyano-N'-methyl-N''-[2-((3-hydroxy-2-pyridyl)methylthio)ethyl]guanidine. | 150 mg. |
| Mepyramine | 75 mg. |
| Sucrose | 75 mg. |
| Starch | 25 mg. |
| Talc | 5 mg. |
| Stearic Acid | 2 mg. |

The ingredients are screened, mixed and filled into a hard gelatin capsule.

EXAMPLE 102

| Ingredients | Amounts |
|---|---|
| N-cyano-N'-methyl-N''-[2-((3-bromo-2-pyridyl)methylthio)ethyl]guanidine. | 200 mg. |
| Mebrophenhydramine | 100 mg. |
| Lactose | 100 mg. |

The ingredients are screened, mixed and filled into a hard gelatin capsule.

What is claimed is:

1. A pharmaceutical composition having H-1 and H-2 histamine receptor inhibiting activity which comprises about 30 mg. to about 250 mg. of an antihistamine, said antihistamine being a compound which inhibits those histamine receptors inhibited by mepyramine, about 50 mg. to about 500 mg. of an H-2 histamine receptor inhibitor, H-2 histamine receptors being those histamine receptors which are not inhibited by mepyramine but are inhibited by burimamide, and a pharmaceutically acceptable diluent or carrier, wherein said H-2 histamine receptor inhibitor is a compound of the formula:

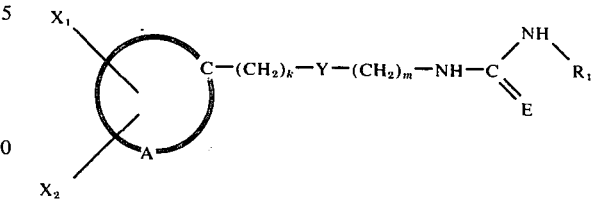

wherein A is such that there is formed together with the carbon atom shown an imidazole ring; $X_1$ is hydrogen, lower alkyl, halogen, amino or hydroxyl; $X_2$ is hydrogen; $k$ is 1; $m$ is 2; Y is sulphur; E is $NR_2$; $R_1$ is hydrogen or lower alkyl; and $R_2$ is hydrogen, nitro or cyano, or a pharmaceutically acceptable acid addition salt thereof.

2. A pharmaceutical composition according to claim 1 wherein the antihistamine is a compound selected from the group consisting of mepyramine, mebrophenhydramine, promethazine, diphenhydramine, chloropheniramin, triprolidene, antazoline, bromodiphenyldramine, parabromdylamine, carbinoxamine, cyproheptadine, chlorcyclizine, dimethindene, diphenylpyraline, dimethothiazine, methdilazine, trimeprazine, mebhydroline, methapyrilene, phenindamine, pheniramine, phenyltoloxamine and pyrrobutamine.

3. A pharmaceutical composition according to claim 1 wherein the H-2 histamine receptor inhibitor is a compound selected from the group consisting of N-cyano-N'-methyl-N''-[2-((4-methyl-5-imidazolyl)-methylthio)ethyl]guanidine, 2-[(4-imidazolyl)methylthio]-ethylguanidine and N-(2-[(4-methyl-5-imidazolyl)methylthio]-ethyl)-N'-nitroguanidine.

4. A pharmaceutical composition according to claim 1 wherein the H-2 histamine receptor inhibitor is N-cyano-N'-methyl-N''-[2-((4-methyl-5-imidazolyl)methylthio)ethyl]guanidine.

5. A pharmaceutical composition according to claim 1, wherein the antihistamine is mepyramine and the H-2 histamine receptor inhbitor is N-cyano-N'-methyl-N''-[2-((4-methyl-5-imidazolyl)methylthio)ethyl]-guanidine.

6. A method of inhibiting H-1 and H-2 histamine receptors which comprises administering to an animal in need thereof, in amount sufficient to inhibit both H-1 and H-2 histamine receptors, an antihistamine, said antihistamine being a compound which inhibits those histamine receptors inhibited by mepyramine, and an H-2 histamine receptor inhibitor, said H-1 histamine receptors being those histamine receptors which are inhibited by mepyramine and said H-2 histamine receptors being those histamine receptors which are not inhibited by mepyramine but are inhibited by burimamide, wherein said H-2 histamine receptor inhibitor is a compound of the formula:

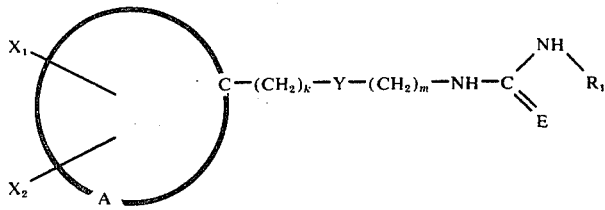

wherein A is such that there is formed together with the carbon atom shown an imidazole ring; $X_1$ is hydrogen, lower alkyl, halogen, amino or hydroxyl; $X_2$ is hydrogen; $k$ is 1; $m$ is 2; Y is sulphur; E is $NR_2$; $R_1$ is hydrogen or lower alkyl; and $R_2$ is hydrogen, nitro or cyano, or a pharmaceutically acceptable acid addition salt thereof.

7. A method of claim 6 wherein the antihistamine is a compound selected from the group consisting of mepyramine, mebrophenhydramine, promethazine, diphenhydramine, chlorpheniramine, triprolidene, antazoline, bromodiphenydramine, parabromdylamine, carbinoxamine, cyproheptadine, chlorcyclizine, dimethindene, diphenylpyraline, dimethothiazine, methdilazine, trimeprazine, mebhydroline, methapyrilene, phenindamine, pheniramine, phenyltoloxamine and pyrrobutamine.

8. A method of claim 6 wherein the H-2 histamine receptor inhibitor is selected from the group consisting of N-cyano-N'-methyl-N''-[2-((4-methyl-5-imidazolyl)methylthio)ethyl]guanidine, 2-[(4-imidazolyl)methylthio]ethylguanidine and N-(2-[(4-methyl-5-imidazolyl)methylthio]ethyl)-N'-nitroguanidine.

9. A method of calim 6 wherein the H-2 histamine receptor inhibitor is N-cyano-N'-methyl-N''-[2-((4-methyl-5-imidazolyl)methylthio)ethyl]guanidine.

10. The method of claim 6 wherein the antihistamine is mepyramine and the H-2 histamine receptor inhibitor is N-cyano-N'-methyl-N''-[2-((4-methyl-5-imidazolyl)methylthio) ethyl]guanidine.

11. A method of producing anti-inflammatory activity which comprises administering to an animal in need thereof, in amounts sufficient to produce said activity, an antihistamine, said antihistamine being a compound which inhibits those histamine receptors inhibited by mepyramine, and an H-2 histamine receptor inhibitor, said H-2 histamine receptors being those histamine receptors which are not inhibited by mepyramine but are inhibited by burimamide, wherein said H-2 -histamine receptor inhibitor is a compound of the formula:

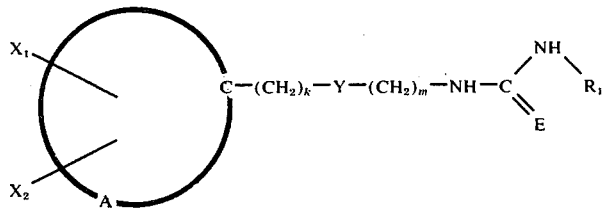

wherein A is such that there is formed together with the carbon atom shown an imidazole ring; $X_1$ is hydrogen, lower alkyl, halogen, amino or hydroxyl; $X_2$ is hydrogen; $k$ is 1; $m$ is 2; Y is sulphur; E is $NR_2$; $R_1$ is hydrogen or lower alkyl; and $R_2$ is hyrodgen nitro or cyano, or a pharmaceutically acceptable acid addition salt thereof.

12. A method of claim 11 in which the antihistamine is a compound selected from the group consisting of mepyramine, mebrophenhydramine, promethazine, diphenhydramine, chlorpheniramine, triprolidene, antazoline, bromodiphenhydramine, parabromdylamine, carbinoxamine, cyproheptadine, chlorcyclizine, dimethindene, diphenylpyraline, dimethothiazine, methdilazine, trimeprazine, mebhydroline, methapyrilene, phenindamine, pheniramine, phenyltoloxamine and pyrrobutamine.

13. A method of claim 11 wherein the H-2 histamine receptor inhibitor is selected from the group consisting of N-cyano-N'-methyl-N''-[2-((4-methyl-5-imidazolyl)methylthio)ethyl]guanidine,2-[(4-imidazolyl)methylthio]ethylguanidine and N-(2-[(4- methyl-5-imidazolyl)methylthio]ethyl)-N'-nitroguanidine.

14. A method of claim 11 wherein the H-2 histamine receptor inhibitor is N-cyano-N'-methyl-N''-[2-((4-methyl-5-imidazolyl)methylthio)ethyl]guanidine.

15. A method of claim 11 wherein the antihistamine is mepyramine and the H-2 histamine receptor inhibitor is N-cyano-N'-methyl-N''-[2-((4-methyl-5-imidazolyl)methylthio)-ethyl]quanidine.

16. A pharmaceutical composition having H-1 and H-2 histamine receptor inhibiting activity which comprises about 30 mg. to about 250 mg. of an antihistamine, said antihistamine being a compound which inhibits those histamine receptors inhibited by mepyramine, about 50 mg. to about 500 mg. of an H-2 histamine receptor inhibitor, H-2 histamine receptors being those histamine receptors which are not inhibited by mepyramine but are inhibited by burimamide, and a pharmaceutically acceptable diluent or carrier, wherein said H-2 histamine receptor inhibitor is 4-(3-guanidinopropyl)imidazole or a pharmaceutically acceptable acid addition salt thereof.

17. A method of inhibiting H-1 and H-2 histamine receptors which comprises administering to an animal in need thereof, in amounts sufficient to inhibit both H-1 and H-2 histamine receptors, an antihistamine, said antihistamine being a compound which inhibits those histamine receptors inhibited by mepyramine, and an H-2 histamine receptor inhibitor, said H-1 histamine receptors being those histamine receptors which are inhibited by mepyramine and said H-2 histamine receptors being those histamine receptors which are not inhibited by mepyramine but are inhibited by burimamide, wherein said H-2 histamine receptor inhibitor is 4-(3-guanidinopropyl)imidazole or a pharmaceutically acceptable acid addition salt thereof.

18. A method of producing anti-inflammatory activity which comprises administering to an animal in need thereof, in amounts sufficient to produce said acitivity, an antihistamine, said antihistamine being a compound which inhibits those histamine receptors inhibited by mepyramine, and an H-2 histamine receptor inhibitor, said H-2 histamine receptors being those histamine receptors which are not inhibited by mepyramine but are inhibited by burimamide, wherein said H-2 histamine receptor inhibitor is 4-(3-guanidinopropyl)imidazole or a pharmaceutically acceptable acid addition salt thereof.

* * * * *

UNITED STATES PATENT AND TRADEMARK OFFICE
CERTIFICATE OF CORRECTION

PATENT NO. : 4,000,302
DATED : December 28, 1976
INVENTOR(S) : James Whyte Black and Michael Edward Parsons It is certified that error appears in the above—identified patent and that said Letters Patent are hereby corrected as shown below:

On the first page of the patent, in the left-hand column, following item [63] insert the following:

[30] Foreign Application Priority Data

April 20, 1972     United Kingdom 18301/72

Column 1, line 56, "antagonits" should read -- antagonist --.

Column 2, line 40, "(45)" should read -- (4(5) --.

Column 7, line 27, "ction" should read -- action --.

Column 7, line 28, "action micromoles" should read -- 500 micromoles --.

Column 36, lines 64-65, "chloropheniramin" should read -- chlorpheniramine --.

Column 36, lines 65-66, "bromodiphenyldramine" should read -- bromodiphenydramine --.

Column 37, line 16, "inhbitor" should read -- inhibitor --.

Column 37, line 21, "amount" should read -- amounts --.

Column 39, line 9, "quanidine" should read -- guanidine --.

Signed and Sealed this

Twenty-second Day of March 1977

[SEAL]

Attest:

RUTH C. MASON
Attesting Officer

C. MARSHALL DANN
Commissioner of Patents and Trademarks